(12) United States Patent
Huang et al.

(10) Patent No.: US 8,444,993 B2
(45) Date of Patent: May 21, 2013

(54) MULTI-PHASE EMULSIONS BASED ON AMPHIPHILIC BLOCK COPOLYMERS

(75) Inventors: Ming-Hsi Huang, Miaoli County (TW); Pele Choi-Sing Chong, Miaoli County (TW); Chih-Hsiang Leng, Miaoli County (TW); Shih-Jen Liu, Miaoli County (TW); Hsin-Wei Chen, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 13/604,610

(22) Filed: Sep. 5, 2012

(65) Prior Publication Data

US 2012/0328654 A1    Dec. 27, 2012

Related U.S. Application Data

(63) Continuation of application No. 12/533,086, filed on Sep. 2, 2009.

(51) Int. Cl.
| | | |
|---|---|---|
| *A61K 39/00* | (2006.01) | |
| *A61K 39/145* | (2006.01) | |
| *A61K 47/30* | (2006.01) | |
| *A61K 39/39* | (2006.01) | |
| *A61K 39/12* | (2006.01) | |

(52) U.S. Cl.
CPC .............. *A61K 39/145* (2013.01); *A61K 39/39* (2013.01); *A61K 39/12* (2013.01); *Y10S 514/937* (2013.01); *Y10S 514/938* (2013.01)
USPC .............. 424/184.1; 424/209.1; 514/772.3; 514/937; 514/938

(58) Field of Classification Search
CPC ..... A61K 39/00; A61K 39/145; A61K 2121/00
USPC ................ 424/184.1, 209.7; 514/772.3, 937, 514/938
See application file for complete search history.

(56) References Cited

U.S. PATENT DOCUMENTS

| | | | | |
|---|---|---|---|---|
| 5,622,649 | A | * | 4/1997 | Hunter et al. .................... 516/29 |
| 2003/0060559 | A1 | | 3/2003 | Oliviere |
| 2007/0191314 | A1 | * | 8/2007 | Klucker et al. ................ 514/102 |
| 2011/0052633 | A1 | * | 3/2011 | Huang et al. ............... 424/209.1 |

OTHER PUBLICATIONS

Treanor et al., The New England Journal of Medicine, 2006, 354(13), 1343-1351.*
Huang et al., J. Biomed Mater Res Part B: Appl Biomater, 2009, 90B, 832-841.*
Jeong et al. (1999) "Thermorevesible Gelation of Poly (Ethylene Oxide) Biodegradable Polyester Block Copolymers" J. of Polymer Science: Part A: Polymer Chemistry, vol. 37, 761-760.
Burt et al. (1999) "Development of copolymers of Poly (D, L-Lactide) and methoxypolyethylene glycol as micellar carriers of paclitaxel" Colloids and Surfaces B: Biointerfaces, 16: 161-171,.

* cited by examiner

*Primary Examiner* — Abigail Fisher
(74) *Attorney, Agent, or Firm* — Hsiu-Ming Saunders; Intellectual Property Connections, Inc.

(57) ABSTRACT

A method for enhancing a body's response to an immunogen is disclosed. The method comprises immunizing a subject in need thereof a vaccine composition in a water-in-oil (W/O/W) emulsion that comprises (a) an antigen; and (b) an adjuvant composition in a W/O/W emulsion. The adjuvant composition comprises: (i) a continuous aqueous phase comprising $H_2O$; (ii) an oil phase comprising oil dispersed in the continuous aqueous phase, comprising an internal aqueous phase comprising $H_2O$, being dispersed in the oil phase; and a physiologically acceptable lipophilic emulsifier selected from the group consisting of mannide monooleate and sorbitan esters, stabilizing the interface between the inner aqueous phase and the oil phase to form a water-in-oil (W/O) emulsion; and (iii) poly(ethylene glycol)-block-poly(lactide-co-ε-caprolactone), stabilizing the interface between the oil phase and the continuous aqueous phase.

18 Claims, 11 Drawing Sheets

(a)

monomethoxy PEG      lactic acid

PLA-PEG diblock copolymer (b)

dihydroxyl PEG      lactic acid

PLA-PEG-PLA triblock copolymer

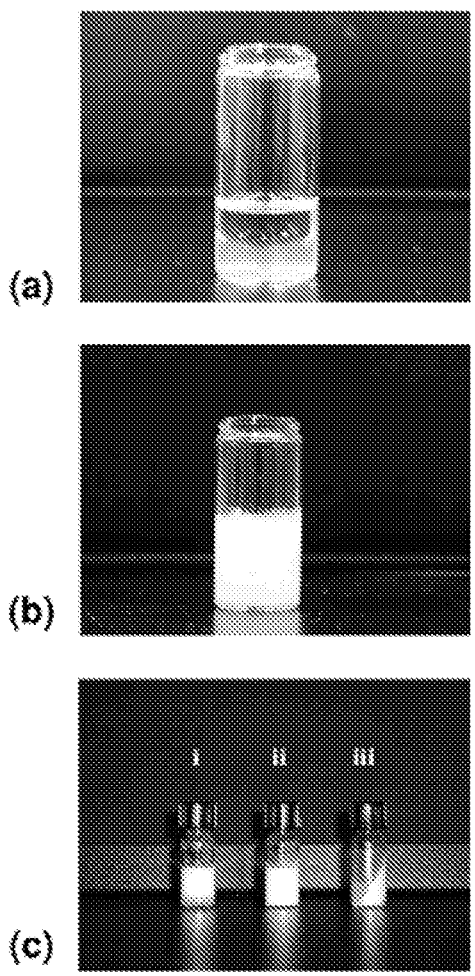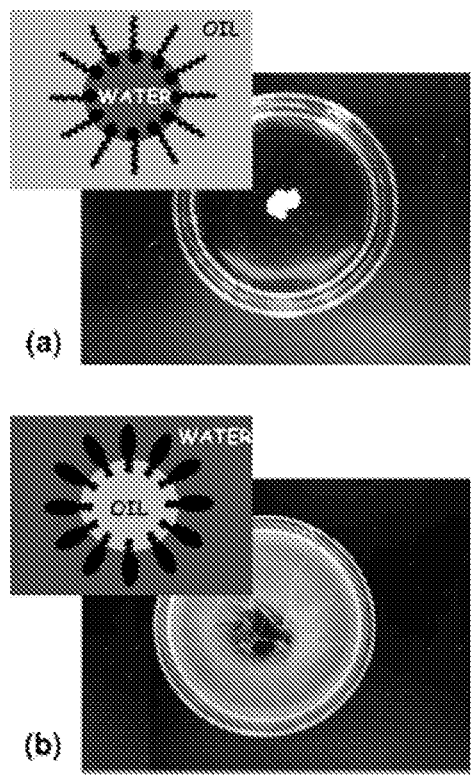
FIG. 8
FIG. 9

MULTI-PHASE EMULSIONS BASED ON AMPHIPHILIC BLOCK COPOLYMERS

REFERENCE TO RELATED APPLICATION

This application is a continuation of and claim priority to U.S. Ser. No. 12/553,086, filed Sep. 2, 2009, which status is pending and is herein incorporated by reference in its entirety.

FIELD OF THE INVENTION

The present invention relates generally to emulsion formulations, and more specifically to a multi-phase emulsion formulations.

BACKGROUND OF THE INVENTION

Among the vaccine adjuvants evaluated in human trials, the emulsion-type adjuvants have the advantages of ease of manufacture and low costs. Freund's adjuvants and MONTANIDE® ISA 51 (ISA51), containing mineral oil and lipophilic emulsifier named mannide monooleate, are defined as water-in-oil (W/O) emulsions with dispersed antigenic media and continuous oily phases. Although the mechanisms of adjuvant's action are poorly understood, the W/O types of adjuvant products have been evaluated to improve the innocuity of the vaccine and to achieve long-term, protective immune responses. It is difficult to give injections with syringe needle having a small diameter. There are also local reactions at the injection site, which limit their applications to humans. To improve the injectability of such vaccines, a method for re-dispersing them in an aqueous phase containing a hydrophilic emulsifier TWEEN® 80 (polyoxyethylene sorbitan monooleate) has been described. Nevertheless, TWEEN® 80 is a lipid dispersant, can attack cell walls and hence is potentially toxic. Preclinical experience has found that TWEEN® 80-stabilized emulsions were generally more immunogenic than non-adjuvanted vaccines but also increased the reactogenicity.

To increase the number of safe emulsifiers for vaccine adjuvants, synthetic polymer is regarded as an interesting alternative to low-molecular weight surfactants (LMWS) because the size and the relative positions of hydrophilic and lipophilic blocks can be easily tailored by the order of the monomer addition and by the amounts of monomer used to produce a broad range of surfactant characteristics. One of the examples is TITERMAX®, in which a squalene-based water-in-oil (W/O) emulsion is stabilized by microparticulate silica and the non-ionic block copolymer polyoxyethylene-polyoxypropylene-polyoxyethylene (POE-POP-POE, known as PLURONIC® or POLOXAMER®). TITERMAX® elicits more potent immune responses than the LMWS-emulsified formulation but its application in human vaccine delivery is still dubious because the stabilizers used are toxic and non-biodegradable.

A heretofore unaddressed need exists in the art to address the aforementioned deficiencies and inadequacies, especially in connection with enhancement of the water affinity of W/O emulsion-adjuvanted vaccines.

SUMMARY OF THE INVENTION

One aspect of the invention relates to a composition comprising:
(a) a continuous aqueous phase comprising $H_2O$;
(b) an oily phase comprising oil; and
(c) an amphiphilic emulsifying system stabilizing the interface between the oily phase and the continuous aqueous phase, comprising a block copolymer having the formula $$(A)p-(B)q-(C)r$$

wherein:
p, q and r are integers with the proviso that:
if p is 1, then A is other than hydroxyl or reactive functional groups and the block copolymer is a diblock copolymer, in which (B)q is a hydrophilic block and (C)r is a hydrophobic block; B and C are each individual repeating units;
if p is >1, then the block copolymer is a triblock copolymer, in which (B)q is a hydrophilic block and (A)p and (C)r are each hydrophobic blocks; the hydrophobic blocks (A)p and (C)r are each homopolymers or heteropolymers; A, B and C are each individual repeating units; the repeating units A and C are the same or different;
and wherein the ratio q/(p+r) is sufficient high so that the hydrophilic-lipophilic balance (HLB) of the block copolymer is >10.

In one embodiment of the invention, the aforementioned composition is dispersed in a phosphate-buffered saline solution (PBS), wherein the composition is in the form of an oil-in-water (O/W) emulsion, and wherein the aqueous phase comprises PBS.

The oily phase may entrap or encapsulate an antigen and/or a bioactive agent. Alternatively, the continuous aqueous phase may comprise an antigen and/or a bioactive substance.

In another embodiment of the invention, the aforementioned composition is free of an organic solvent.

In another embodiment of the invention, the oily phase further comprises an emulsion comprising:
(a) an internal aqueous phase comprising $H_2O$, being dispersed in the oily phase; and
(b) a lipophilic emulsifying system stabilizing the interface between the inner aqueous phase and the oily phase to form a water-in-oil (W/O) emulsion;
wherein the composition is in the form of a W/O/W emulsion.

in another embodiment of the invention, the lipophilic emulsifying system comprises at least one physiologically acceptable emulsifier selected from the group consisting of mannide monooleat and sorbitan esters.

The W/O/W emulsion formulation may further comprise an antigen and/or a bioactive agent dissolved in the internal aqueous phase and/or in the continuous aqueous phase. The antigen may be an inactivated virus, e.g., H5N1 virus, or a bacterium and/or an antigenic protein or an antigenic fusion protein.

In another embodiment of the invention, the inner aqueous phase further comprises an antigen and/or a bioactive agent.

Another aspect of the invention relates to a block copolymer comprising the formula:

$$(A)p-(B)q-(C)r$$

wherein:
p, q and r are integers with the proviso that:
if p is 1, then A is other than hydroxyl or reactive functional groups and the block copolymer is a diblock copolymer, in which (B)q is a hydrophilic block and (C)r is a hydrophobic block; B and C are each individual repeating units;
if p is >1, then the block copolymer is a triblock copolymer, in which (B)q is a hydrophilic block and (A)p and (C)r are each hydrophobic blocks; the hydrophobic blocks (A)pr and (C)r are each homopolymers or heteropolymers; A, B and C are each individual repeating units; the repeating units A and C are the same or different;

and wherein the ratio q/(p+r) is sufficient high so that the hydrophilic-lipophilic balance (HLB) value of the block copolymer is >10.

In one embodiment of the invention, the hydrophilic block (B)q constitutes at least 50% by weight of the block copolymer.

In one embodiment of the invention, p is 1 and A is methoxy.

In another embodiment of the invention, the block copolymer is bioresorbable.

In another embodiment of the invention, the hydrophilic block (B)q is a liner polymer.

In another embodiment of the invention, the repeating unit B is selected from the group consisting of ethylene oxide, vinylpyroolidone, and acrylamide.

In another embodiment of the invention, the hydrophobic blocks (A)p and (C)r are each polyester polymers.

Further in another embodiment of the invention, the hydrophobic blocks (A)p and (C)r are each aliphatic polyesters.

In another embodiment of the invention, the repeating units A and C are each selected from the group consisting of hydroxyacids, lactones, and combinations thereof.

The hydroxyacids may be selected from the group consisting of lactic acid, 6-hydroxycaproic acid, glycolic acid, malic acid monoesters, and combinations thereof.

The lactones may be selected from the group consisting of ε-caprolactone, lactide, glycolide, para-dioxanones, and combinations thereof.

In another embodiment of the invention, the aliphatic polyesters are polymers of dicarboxylic acids and a diols.

In another embodiment of the invention, the hydrophobic blocks (A)p and (C)r are each comprises a polymer selected from the group consisting of the following:
  (i) a hydroxyacid-containing polymer: poly(lactide), poly (lactic acid), poly(lactide-co-glycolide), poly(glycolide), poly(lactic acid-co-glycolic acid), poly(malic acid), poly(malic acid ester), or poly(glycolic acid);
  (ii) a lactone-containing polymer: poly(lactide-co-ε-caprolactone), poly(ε-caprolactone), or poly(glycolide-co-ε-caprolactone); and
  (iii) a hydroxycaproic acid-containing polymer: poly(acetic acid-co-6-hydroxycaproic acid), or poly(glycolic acid-co-6-hydroxycaproic acid).

Yet in another embodiment of the invention, the block copolymer is selected from the group consisting of poly(ethylene glycol)-block-poly(lactide-co-ε-caprolactone), poly (ethylene glycol)-block-polylactide, and poly(ethylene glycol)-block-poly(ε-caprolactone).

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 8(a)-8(c) are photographs showing polymer/oil emulsions (a) before and (b) after homogenization at 6000 rpm for 5 min, and (c) the visual aspects of the emulsions stored at 4° C. for two months. The polymer concentration in the antigen medium aqueous solution was 13 wt % and the aqueous/oily solution was 5/5 w/w. (i) PEG-b-PLACL/squalene, (ii) PEG-b-PLACL/squalene/SPAN® 85, (iii) PBS/squalene/SPAN® 85.

FIGS. 9(a)-9(b) are photographs showing the results of droplet tests of the emulsion formulations (a) PBS/squalene/SPAN® 85 and (b) PEG-b-PLACL/squalene.

the C/W emulsion PEG-b-PLACL/Squalene, (open triangle) the W/O/W emulsion PEG-b-PLACL/squalene/SPAN® 85 (filled circle) the W/O emulsion PBS/squalene/SPAN® 85. The OVA-containing formulations (3 mg per 0.3 mL) were placed in a dialysis chamber in a centrifuge tube containing 2 mL, of PBS and stood at 37° C. The OVA release was monitored by the BCA method and read by an UV-vis instrument at 562 nm using calibration curves obtained from the standard BSA solutions (2, 1, 0.5, 0.25, 0.125 mg/mL). The data are presented as the mean with standard errors of three samples.

FIG. 11(b) is photograph showing the recovered formulations after the experiments in FIG. 11(a).

Figure 12:
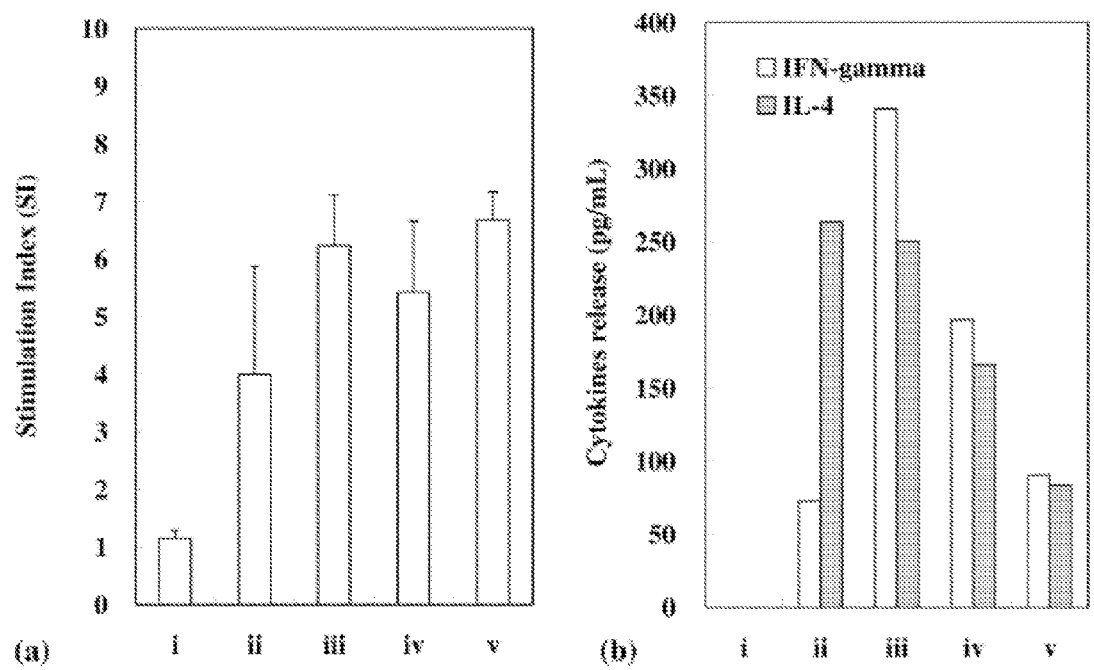

FIGS. 12(a)-12(b) show (a) T-cell proliferation and (b) cytokine release responses in spleen cells from mice immunized with OVA in different formulations with or without adjuvants. (i) control; (ii) no adjuvant; (iii) PEG-b-PLACL/squalene; (iv) PEG-b-PLACL/squalene/SPAN® 85; (v) aluminum phosphate. The BALB/c mice were vaccinated subcutaneously at week 0 with 0.5 µg of OVA and boosted at weeks 2 and 4. One week after the final boost, splenocyte suspensions from a pool of two mice per group were prepared for cytokines assay and incubated over five days with or without 10 µg/mL of antigen OVA. The stimulation index (SI) is the ratio of the mean counts per minute (c.p.m.) in the presence of the antigen to the c.p.m. in the absence of the antigen. Results are expressed as the mean with standard errors (n=3). Proliferation was read as positive when the SI values were >2. Supernatants collected from triplicate cultures were measured by IFN-γ and IL-4 cytokine ELISA paired antibodies. Data are presented as cytokine release in the presence of OVA minus that with medium only (n=3).

Figure 13:
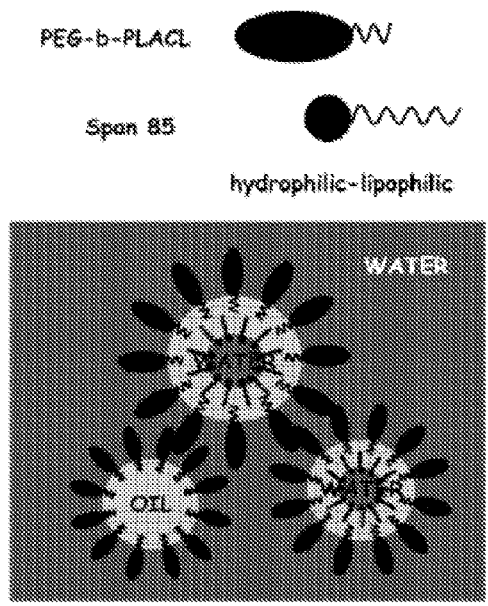

FIG. 13 is a schematic representation of a W/O/W emulsion. The emulsion PEG-b-PLACL/squalene/SPAN® 85 comprises two surfactants. PEG-b-PLACL and SPAN® 85, rendering a W/O/W multi-phase emulsion, in which the oil droplets were dispersed in the continuous water, but the core oil also traps an internal aqueous phase.

Figure 14:
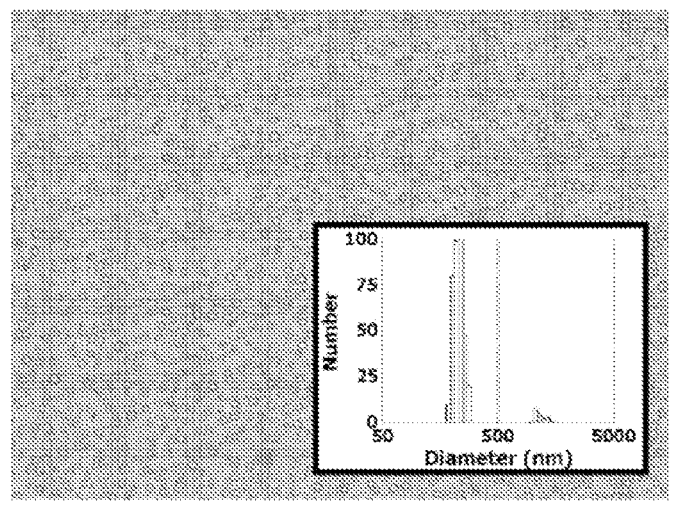

FIG. 14 shows a PELC-formulated influenza vaccine having homogeneous fine particles with diameters ranging from 200 to 400 nm. The inset is a histogram showing the particles' size distribution.

Figure 15A:
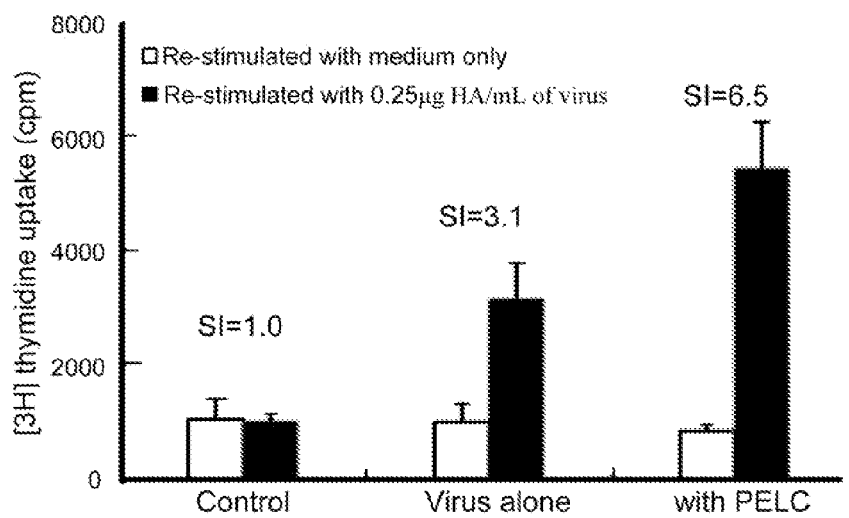

FIG. 15A is a graph showing T-cell proliferation in the splenocytes of mice immunized with inactivated H5N1 virus alone or with PELC. The BALB/c mice were vaccinated i.m. with a single-dose of 0.5 µg of viral HA. Twelve days after immunization, splenocyte suspensions were pooled from three mice per group and incubated for four days with or without 0.25 µg HA/mL of antigen. The Stimulation Index (SI) is the ratio of the mean counts per minute (cpm) with antigen to the cpm without antigen. The data are expressed as the mean plus the standard deviation (n=3). Proliferation was deemed positive when the SI value was >3.

Figure 15B:
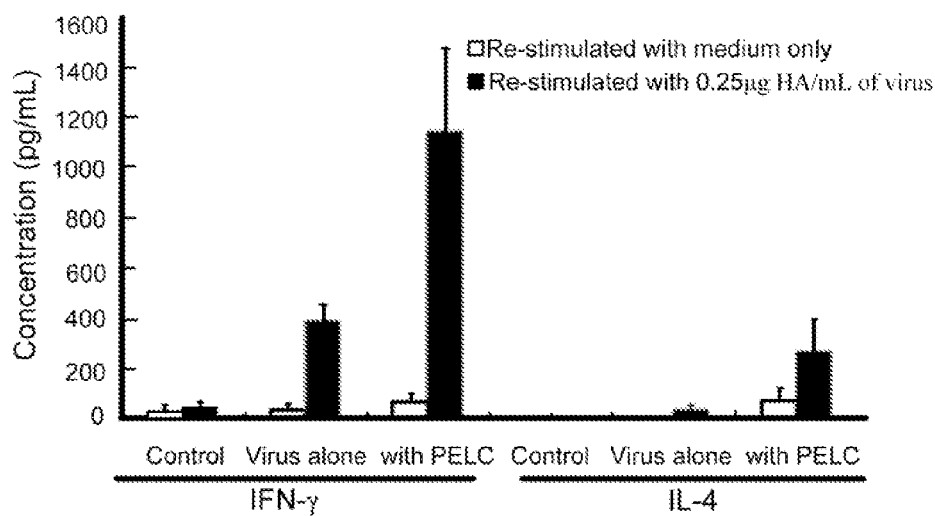

FIG. 15B is a graph showing cytokines release from the splenocytes. The supernatants collected from the triplicate cultures in FIG. 15A were assessed with IFN-γ and IL-4 ELISA. The data are expressed as the mean plus the standard errors (n=3).

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "immunity adjuvants" shall generally mean products which increase the reactions of the immunity system when they are administered in the presence of antigen of virus, bacterial or synthetic origin.

As used herein, the term "biodegradable" shall generally mean solid polymeric materials which break down due to macromolecular degradation with dispersion in vivo but no proof for the elimination from the body (this definition excludes environmental, fungi or bacterial degradation). Biodegradable polymeric systems can be attacked by biological elements so that the integrity of the system, and in some cases but not necessarily, of the macromolecules themselves is affected and gives fragments or other degradation by-products. Such fragments can move away from their site of action but not necessarily from the body.

As used herein, the term "bioresorbable" shall generally means solid polymeric materials which show bulk degradation and further resorb in vivo; i.e., polymers which are eliminated through natural pathways either because of simple filtration of degradation by-products or after their metabolization. Bioresorption is thus a concept which reflects a total elimination of the initial foreign material and of bulk degradation by-products (low molecular weight compounds) with no residual side effects. The use of the word 'bioresorbable' assumes that the elimination, is shown conclusively (Dietmar W. Hutmacher (2000) "Scaffolds in tissue engineering bone and cartilage" *Biomaterials* 21:2529-2543, which is herein incorporated by reference in its entirety).

As used herein, a "lactone" is a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the latter. A "lactide" is a cyclic diester of lactic acid, i.e., a di-lactone, A "glycolide" is a cyclic diester of glycolic acid, which is also a di-lactone.

As used herein, "dicarboxylic acids" are organic compounds that are substituted with two carboxylic acid functional groups, such as succinic acid.

As used herein, a "diol" or "glycol" is a chemical compound containing two hydroxyl groups (—OH groups), such as ethylene glycol.

As used herein, a "hydroxy acid" is an organic compound which contains a carboxylic acid functional group and hydroxy functional group.

As used herein, the term "amphiphile" means any organic compounds composed of hydrophilic and hydrophobic portions.

As used herein, the term "the ratio q/(p+r) is sufficient high" means that the block copolymer of the formula of (A)p–(B)q–(C)r has a hydrophilic-lipophilic balance (HLB) greater than 10 so that it promotes an oily phase to disperse in an aqueous phase and result in an oil-in-water (O/W) emulsion. For example, the HLB of the amphiphile block copolymer may be greater than 10, 11, 12, 13, 14, 15, 16, 17, 18, or near 20.

As used herein, the term "A is other than a reactive functional group or a reactive group" refers to any group that does not react under conditions where the non-protected group reacts. In this case, the group "A" protects reactive functional groups, such as hydroxyl or amino groups, from their reaction with growing species in polymerization.

As used herein, the term "hydroxy-protecting group" refers to any group commonly used for the protection of hydroxy functions during subsequent reactions, including, for example, alkoxyl, acyl or alkylsilyl groups such as trimethylsilyl, triethylsilyl, t-butyldimethylsilyl and analogous alkyl or arylsilyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical or 1 to 10 carbons in all its isomeric forms, such as methyl, ethyl, propyl, isopropyl, butyl, isobutyl, pentyl, etc., and the terms "hydroxy-alkyl," "fluoroalkyl" and "deuteroalkyl" refer to such an alkyl radical substituted by one or more hydroxy, fluoro or deuterium groups, respectively. An "acyl" group is an alkanoyl group of 1 to 6 carbons in all its isomeric forms, or an aroyl group, such as benzoyl, or halo-, nitro-, or alkyl-substituted benzoyl groups, or an alkoxycarbonyl group of the type Alkyl-O—CO—, such as methoxycarbonyl, ethoxycarbonyl, propyloxycarbonyl, etc., or a dicarboxylic acyl group such as oxalyl, malonyl, succinoyl, glutaroyl, or adipoyl. The term "aryl" signifies a phenyl-, or an -alkyl-, nitro-, or halo-substituted phenyl group. The term alkoxy signifies the group, alkyl-O—.

The full names for abbreviations used herein are as follows: $^1$H NMR, $^1$H nuclear magnetic resonance; APCs, antigen-presenting cells; BCA, bicinchinonic acid; ELISA, enzyme-linked immunosorbent assay; FDA, Food and Drug Administration; GPC, gel permeation chromatography; HLB, hydrophilic-lipophilic balance; IgG, immunoglobulin GPC; ISA51, MONTANIDE® ISA 5 oil adjuvant; LMWS, low-molecular weight surfactants; MALDI-TOF MS, matrix-assisted laser desorption/ionization time of flight mass spectrometry; MePEG$_{5000}$, Poly(ethylene glycol) 5,000 monomethyl ether; $\overline{Mn}$, number average molecular weight; $\overline{Mw}/\overline{Mn}$, molecular weight distribution; OVA, ovalbumin; O/W, oil-in-water; PBS, phosphate buffered saline; PBS/ISA 51, PBS dispersed in ISA 51 emulsion; PEG-b-PCL, poly(ethylene glycol)-block-poly(ε-caprolactone); PEG-b-PLA, poly(ethylene glycol)-block-polylactide; PEG-b-PLACL, poly(ethylene glycol)-block-poly(lactide-co-ε-caprolactone); PEG-b-PLACL/ISA51/PBS, PEG-b-PLACL-stabilized ISA51 emulsion following dispersed in PBS; POE-POP-POE, polyoxyethylene-polyoxypropylene-polyoxyethylene, s.c., subcutaneous; SnOct$_2$, Tin(II) 2-ethylhexanoate; THF, tetrahydrofuran; TMB, tetramethylbenzidine; TWEEN® 80, polyoxyethylene sorbitan monooleate; W/O, water-in-oil; W/O/W, water-in-oil-in-water.

Emulsifiers may be defined by their hydrophilic-lipophilic balance (HLB) values, which give information on their relative affinity for aqueous and oily phases. An emulsifying system which contains an emulsifier of low HLB value renders a W/O emulsion with a high affinity for an oily phase. In contrast, an emulsifying system which contains a high HLB value affords an O/W emulsion with a high affinity for an aqueous phase. A W/O/W multi-phase emulsion may be achieved when an emulsifying system contains an intermediate HLB value. These parameters, however, are strongly influenced by the optimization of a surfactant system and the manufacture process.

For an emulsifier system comprising one or more emulsifiers, the HLB is calculated based on the following equation:

$$HLB_{mix} = \Sigma X_i \times HLB_i$$

where X is the weight fraction of surfactant i.

For non-ionic surfactants, HLB may be calculated with the Griffin's method:

$$HLB = 20 \times M_h/M$$

where $M_h$ is the molecular mass of the hydrophilic portion of the molecule, and M is the molecular mass of the whole molecule. The HLB of the most lipophilic molecule is close to 0, while the HLB of the most hydrophilic molecule is about 20.

For a non-ionic copolymer, the equation can be represented as follows:

$$HLB_{copolymer} = 20 \times W_h/W_{copolymer}$$

where $W_h/W_{copolymer}$ is the weight ratio of the hydrophilic portion of the main chain polymer and is obtained from their number average molecular weight ratio $\overline{Mn}_h/\overline{Mn}_{copolymer}$.

A W/O emulsion based on lipophilic mannide monooleate and water-immiscible oil has been available. The oil used is the mineral oil Markol (Freund's adjuvants), metabolizable mineral oil Drakeol (MONTANIDE® ISA 51) or metabolizable nonmineral squalene (MONTANIDE® ISA 720). TITERMAX® is a squalene-based W/O emulsion stabilized by microparticulate silica and the nonionic block copolymer polyoxyethylene-polyoxypropylene-polyoxyethylene (POE-POP-POE, known as PLURONIC® or POLOXAMER®). These W/O emulsions are difficult for injection with a syringe having a needle of small diameters, and cause local reactions at the injection site of animals, which considerably restrained the potential of this type of emulsions for human use.

The invention relates to formulations for enhancing the water affinity oil-in-water emulsions, such as oily adjuvanted vaccines. We designed different types of emulsion formulations using block copolymers having the formula $$(A)p-(B)q-(C)r$$

Wherein:
  p, q and r are integers with the proviso that:
  if p is 1, then A is other than hydroxyl or reactive functional groups and the block copolymer is a diblock copolymer, in which (B)q is a hydrophilic block and (C)r is a hydrophobic block; B and C are each individual repeating units;

if p is >1, then the block copolymer is a triblock copolymer, in which (B)q is a hydrophilic block and (A)p and (C)r are each hydrophobic blocks; the hydrophobic blocks (A)p and (C)r are each homopolymer or heteropolymer; A, B and C are each individual repeating units; the repeating units A and C are the same or different.

The HLB is sufficient high so that the block copolymer is capable of stabilizing the interface between an oil phase and an aqueous phase and promotes the dispersion of the oil phase into the aqueous phase and forms a stable O/W emulsion. This is particular useful in redispersing an ISA51-adjuvanted oily vaccine, a W/O emulsion, into a PBS to form a W/O/W multiphase emulsion.

In one embodiment of the invention, q is an integer and the hydrophilic portion (B)q has a molecular weight of from about 550 to about 10,000 daltons, preferably from about 2,000 to about 8,000 daltons, and the ratio q/(p+r) is sufficient high so that the hydrophilic portion (B)q constitutes from about 50 to about 95% by weight of the main chain polymer (A)p–(B)q–(C)r, which renders the hydrophilic-lipophilic balance (HLB) of the block copolymer ranging from about 10 to about 19. Preferably the hydrophilic portion (B)q constitutes from about 70 to about 95% by weight of the main chain polymer so that the HLB value ranges from about 14 to about 19.

The ratio of q versus p+r is important for the HLB of amphiphilic macromolecules. If q/(p+r) is not high enough, then the macromolecules do not dissolve in water. For illustration purpose Tables A and B list the block copolymers' molar ratios, q/(p+r), and HLB values (See Huang et al. (2009) "Development of Multi-Phase Emulsions Based on Bioresorbable Polymers and Oily Adjuvant" *Pharmaceutical Research* 26(8): 1856-1862; Huang et al., (2004) Degradation and cell culture studies on block copolymers prepared by ring opening polymerization of ε-caprolactone in the presence of poly(ethylene glycol). *J Biomed Mater Res* 69A: 417-427, which is herein incorporated by reference in its entirety). In an extreme case where the HLB of a block copolymer is 20, the main chain polymer would consist of only a hydrophilic block and the polymer would not possess amphiphilic property. (See Siao et al., (2009) "Characterization and Emulsifying Properties of Block Copolymers Prepared from Lactic Acid and Poly(ethylene glycol)" *Journal of Applied Polymer Science* 114: 509-516, which is herein incorporated by reference in its entirety).

TABLE A

| | [LA]/[CL]/[OE] | q/(p + r) | % of hydrophilic portion | HLB |
|---|---|---|---|---|
| PEG-b-PLA | 0.243/—/1 | 4.1 | 72% | 14.4 |
| PEG-b-PCL | —/0.166/1 | 6.0 | 70% | 14.0 |
| PEG-b-PLACL | 0.100/0.068/1 | 6.0 | 75% | 15.0 |

TABLE B

| | [CL]/[OE] | q/(p + r) | % of hydrophilic portion | HLB |
|---|---|---|---|---|
| PCL-PEG | 3.9/1 | 0.256 | 9% | 1.8 |
| PCL-PEG-PCL | 3.7/1 | 0.270 | 9.5% | 1.9 |
| OCL-PEG | 0.03/1 | 33.3 | 93.5% | 18.7 |
| OCL-PEG-OCL | 0.04/1 | 25.0 | 91.5% | 18.2 |

PCL stands for poly(ε-caprolactone).
OCL stands for oligo(ε-caprolactone).

The oil must be non-toxic, metabolizable, physiologically acceptable, and form fluid emulsions when stored at 4° C. Oils are selected from mineral oils, vegetable or animal oils known for low toxicity. The selected mineral oils may be straight chain mineral oils, e.g., Markol (Freund's adjuvants) or Drakeol (MONTANIDE® ISA 51). Synthetic hydrocarbons include polyisobutene and polyisoprene. Suitable vegetable oils include oleic type unsaturated oils that are biodegradable and known for immunogenic power, such as groundnut oil, olive oil, sesame oil, soya bean oil, corn oil, and jojoba oil, etc. Suitable animal oils require the same criteria of tolerance and immunological efficiency, such as squalane and squalene (MF59®, AS03, MONTANIDE® ISA 720, TITERMAX).

The polymer blocks (A)p and (C)r are hydrophobic linear polyester blocks, e.g., aliphatic polyesters. Aliphatic polyesters may be obtained as follows: a) either by self-polycondensation of a hydroxyacid (i.e., homopolymers), or by polycondensation of different hydroxyacids (i.e., heteropolymers); b) by the polymerization via ring-opening of lactones; and c) by polycondensation of diacids and diols.

Hydroxyacid monomers may be chosen from lactic acid, glycolic acid, 6-hydroxycaproic acid, malic acid monoesters, e.g., alkyl or aralkyl monoesters, or monoesters resulting from the monoesterification of malic acid with a hydroxylated active compound, in particular a hydrophobic active compound; lactides (D-lactide, L-lactide, DL-lactide, and meso-lactide), glycolide, ε-caprolactone, para-dioxanone, and the like. The hydrophobic polymer blocks (A)p and (C)r may be copolymers formed by the polymerization of different monomers.

The optimal length of (A)p and (C)r chains may be determined. The polymer was added to PBS in the presence of the water-insoluble dye diphenylhexatriene, which would dissolve in the hydrophobic core of polymeric micelles or aggregates. After sonication and centrifugation, we observed an abrupt enhancement in the ultraviolet (356 nm) absorption of the dye, which indicated micelle formation.

The polymeric emulsifiers of the invention exhibit distinguishing features. They are biodegradable and bioresorbable. Degradation studies on these copolymers have shown that the polyester chains (A)p and (C)r are gradually degraded by hydrolysis. The final products are corresponding hydroxyacids (or diacids and diols), which are bioresorbable. Continuing hydrolysis will eventually release the hydrophilic polyester chain (B)q, the central block of the copolymer. Such polymers of relatively low molecular mass (less than 10,000) are bioresorbable and may be excreted from the kidney.

The preparation of a W/O/W emulsion requires two factors: a two-step preparation process and an emulsifier with an intermediate HLB value. The Novartis MF59® adjuvant (an O/W submicron emulsion), which contains 4.3% squalene, 0.5% TWEEN® 80 (HLB$_{TWEEN®80}$=15) and 0.5% SPAN® 85 (HLB$_{SPAN®85}$=1.8) as emulsifiers, is prepared via a single-step manufacture process through a microfluidizer at an internal pressure of 12,000 psi, followed by filtration through a 0.22-μm filter membrane to achieve small, stable O/W submicron emulsion particles. The GSK ASO3 adjuvant, which contains 2.5% squalene, 0.9% TWEEN® 80 and 2.5% α-tocopherol, is prepared via a two-step manufacture process, in which a pre-emulsified stock comprising squalene, TWEEN® 80, and alpha-tocopherol was mixed with a bulk antigen before injection, resulting in a fluid O/W emulsion. It however lacks an emulsifying system with an intermediate HLB value.

In another aspect, the invention relates to a process for making a multi-phase W/O/W emulsion, which may trap and/or encapsulate antigens and/or bioactive substances in the multi-phase emulsion. The process comprises a homogenizing (or called emulsifying) step and a diluting (or called dispersing) step. In the homogenizing (or emulsifying) step, a pre-emulsified stock comprising an oil and emulsifiers is obtained, in which a designed block copolymer serves as a hydrophilic emulsifier to stabilize an oil-water interface, and a lipophilic emulsifier serves to stabilize a water-oil interface and result in a stable and isotropic W/O/W emulsion. The W/O/W multi-phase emulsion is achieved with an emulsifying system containing the designed block copolymer with an intermediate HLB value. The oil droplets are dispersed in a continuous aqueous phase, in which the oil-water interface is stabilized by the block copolymer (HLB>>10). In addition, the core oil entraps an aqueous phase, in which the entrapped water-oil interface is stabilized by a lipophilic emulsifier (HLB<<10).

In the diluting (or dispersing) step, the above pre-emulsified stock was diluted by redispersing it into an aqueous solution. The aqueous solution may be an aqueous medium alone, such as PBS, or an aqueous medium containing an antigen or a bioactive substance such as peptides, anticancer agents, hormones, or other active agents such as antibiotics or antiparasitics. The antigen or the bioactive substance may be incorporated into the multiphase emulsion via dissolving in either the oily or the aqueous phase. A water-soluble bioactive substance may be dissolved either in the internal and/or external aqueous phase of the W/O/W emulsion. For a controlled release formulation, dissolving and encapsulating an antigen in the internal aqueous phase has the effect of protecting the antigen. Conversely, dissolving and entrapping an antigen in the external aqueous phase has the effect of facilitating the expression of the antigen.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

This example illustrates the incorporation of hydrophilic polymeric emulsifiers, namely, poly(ethylene glycol)-block-polylactide (PEG-b-PLA), poly(ethylene glycol)-block-poly (ε-caprolactone) (PEG-b-PCL), and poly(ethylene glycol)-block-poly(lactide-co-ε-caprolactone) (PEG-b-PLACL) in the antigen medium to alter the water affinity of oily ISA51-adjuvanted vaccines. These amphiphilic block copolymers were selected because of their biocompatibility and bioresorbability. Various physiochemical properties of emulsions have been characterized, namely, stability, the droplet test, particle size distribution, and in vitro release of a model protein ovalbumin (OVA). Finally, a preliminary immunogenicity evaluation of OVA after formulation with the PEG-b-PLACL-stabilized ISA51 adjuvant was determined in mice for induction of antibody responses in comparison with non-formulated OVA and conventional ISA51 oily adjuvant-formulated OVA (Huang et al. (2009) "Development of Multi-Phase Emulsions Based on Bioresorbable Polymers and Oily Adjuvant" *Pharmaceutical Research* 26(8): 1856-1862, which is herein incorporated by reference in its entirety).

Materials and Methods

Polymer Synthesis and Characterization

Tin(II) 2-ethylhexanoate (stannous octoate, $SnOct_2$) was purchased from Sigma (St. Louis, Mo., USA). DL-lactide (a cyclic di-ester of lactic acid) was purchased from Aldrich (Seelze, Germany) and recrystallized from ethyl acetate. ε-Caprolactone was purchased from Aldrich. Poly(ethylene glycol) 5,000 monomethyl ether ($MePEG_{5000}$) was purchased from Fluka (Buchs, Switzerland). All solvents were of analytical grade.

PEG-b-PLACL was synthesized by ring-opening polymerization of lactide and ε-caprolactone, using $SnOct_2$ as a catalyst and $MePEG_{5000}$ as an initiator. Briefly, a predetermined amount of $MePEG_{5000}$ (2.1 g) lactide (0.58 g), and ε-caprolactone (0.47 g) were placed in a dried round-bottomed bottle, and an appropriate amount of $SnOct_2$ (30 mg) was added as a solution in dried toluene (10 mL). Polymerization was performed at 140° C. under reflux for 24 hr. The product was recovered by precipitation in an excessive amount of ethanol. PEG-b-PLA or PEG-b-PCL was synthesized in the same manner with MePEG/lactide or MePEG/ε-caprolactone at a weight ratio of 2/1.

The resulting polymers were characterized by $^1H$ nuclear magnetic resonance ($^1H$ NMR) and gel permeation chromatography (GPC). $^1H$ NMR spectra were recorded at room temperature with a Varian VXR 300 MHz spectrometer (Varian, Palo Alto, Calif., USA) using deuterated chloroform as the solvent. GPC was performed by using a setting composed of a Waters 510 HPLC pump, a Waters 410 differential refractometer, one PLgel mixed-C 5 μm 100 Å column (7.5× 300 mm), and one PLgel 3 μm 100 Å column (7.5×300 mm), and the mobile phase being tetrahydrofuran (THF) and the flow rate 0.8 mL/min. Data were expressed with respect to polystyrene standards from Polysciences.

Polymer-Stabilized Emulsions

The antigen medium was prepared with a particular concentration of ovalbumin (OVA, Grade V, Sigma, St. Louis, Mo., USA) diluted in a phosphate-buffered saline (PBS). An aqueous solution containing 120 mg of polymer and 0.8 mL of antigen medium and an oil solution containing 1.1 mL of ISA51 (Montanide® ISA 51 F VG, SEPPIC, Paris, France) were emulsified using a Polytron® PT 3100 homogeniser (Kinematica. AG, Swiss) under 6,000 rpm for 5 min. A polymer-free PBS/ISA51 emulsion composed of 0.9 mL of antigen medium and 1.1 mL of ISA51 was also prepared at 8,000 rpm for 10 min. These emulsified formulations served as stocks for further physicochemical characterizations namely stability, the droplet test, particle size distribution and in vitro release.

The stability test was performed by placing each sample at 4° C. and 37° C., and then noted the visual aspect at a predetermined time. The droplet test was assessed by placing a droplet (20 μL) of an emulsion into the water in a beaker (200 mL). The particle size distribution was determined by using the laser light scattering technique with a Brookhaven 90 plus particle sizer (Brookhaven Instruments Limited, New York, USA). In vitro release experiments were performed by using the inverted dialysis tube method. OVA-containing formulations (3 mg per 0.3 mL) were first placed in a dialysis chamber (cutoff 0.2 μm) and then the device was immersed in a 50 mL centrifuge tube containing 2 mL of PBS at 37° C. At different time intervals, 100 μL of sample were aspirated from the medium outside of the chamber and replaced with 100 μL of PBS buffer. The OVA release was regularly determined by the bicinchinonic acid method (BCA™ protein assay kit, Pierce, Rockford, Ill., USA).

Immunization and ELISA Immunoassay

Five-week old female BALB/c mice were obtained from the National Laboratory Animal Breeding and Research Center (Taipei, Taiwan) an) a acclimatized for at least one week at the animal facility of National Health Research Institutes (NHRI, Miaoli, Taiwan) prior to use. All animal studies were approved by the Animal Committee of NHRI. Mice were primed subcutaneously (s.c.; 100 µL) with a syringe needle of 27G×½" and 0.5 µg of OVA in PBS or formulated with PEG-b-PLACL/ISA51 or PBS/ISA51, and boosted with the same formulation at week 2. To increase the fluidity, the group of PEG-b-PLACL/ISA51 was investigated by re-dispersing 100 µL of stock emulsion (See "MATERIALS AND METHODS" SECTION: Polymer-stabilized emulsions) into 900 µL of PBS before injection, resulting in a PEG-b-PLACL/ISA51/PBS emulsion of only 5% oil solution.

To determine the antibody response, mice were bled at the lateral tail vein and the collected sera were stored at −30° C. The presence of OVA-specific antibodies in the sera was determined by enzyme-linked immunosorbent assay (ELISA). Briefly, 100 µL of diluted OVA (10 µg/mL) were coated onto 96-well microtiter plates with 0.05 M carbonate buffer (pH 9.6). After the overnight incubation at 4° C., coated plates were washed twice with PBS containing 0.05% TWEEN® 20 (Sigma, St. Louis, USA) and then blocked with 5% non-fat milk in PBS at room temperature for 2 hr. Diluted sera (starting dilution 1:50, serial three-fold serum dilutions) from immunized animals were applied to wells at room temperature for 2 hr. Following the addition of HRP-conjugated goat anti-mouse IgG (ICN Cappel, Aurora, Ohio, USA), the assay was developed with a substrate solution containing tetramethylbenzidine TMB, SureBLUE™, KPL, MD, USA), and the reaction was stopped in 2 N $H_2SO_4$. Plates were read at 450 nm using an ELISA plate reader (Molecular Devices, Sunnyvale, Calif., USA). The titers were determined based on the reciprocal of the final dilution that gave 2-fold greater absorbance than the pre-immune sera. For isotype determination, 100 µL of an appropriate dilution (1:2,000) of HRP-rabbit anti-mouse IgG1 (ZYMED®, CA, USA) or HRP-rabbit anti-mouse IgG2a (ZYMED®, CA, USA) was added. Statistical significance (p<0.005) was determined by performing two-tailed Student's t-test on log-transformed values.

Results and Discussion

Polymer Design and Characterization

AB-type diblock copolymers consisting of a polyether block (PEG) and a polyester block (PLA, PCL or PLACL) were synthesized by ring-opening polymerization of lactide and/or ε-caprolactone in the presence of MePEG, using $SnOct_2$ as a catalyst. The molecular characteristics of the three copolymers are summarized in Table 1. In this study, MePEG with a molecular weight of 5,000 and an initial hydrophilic/lipophilic ratio of 2/1 were selected as a compromise between the high hydrophilicity of polymers and the bioresorbability of PEG-rich degradation products. In fact, PEG is a water-soluble polymer, particularly, low molecular weight PEG (<10,000 Daltons) can be excreted through kidney filtration. The lipophilic block was derived from the U.S. Food and Drug Administration (FDA)-approved aliphatic polyesters, PLA and PCL. They show bulk degradation and further resorb in vivo. PLA with a variable chain stereoregularity provides a worthwhile means to adjust the rate of degradation. On the other hand, the degradation products of PCL had a relatively higher pKa than those of poly(lactide-co-glycolide) (4.8 for ε-hydroxycaproic acid, and 3.8 for lactic acid and glycolic acid at 25° C.), and they may provide more conservation of protein molecular integrity when being used for a long-term controlled delivery of proteins. PLACL was chosen as the lipophilic block for its fast degradation characteristics. In addition, its amorphous nature provides a good affinity between the polymer matrix and oil solutions. On the selection of catalyst, $SnOct_2$ has been approved by the U.S. FDA for biomedical and therapeutic applications.

TABLE 1

| | | Product | | | | | | | |
|---|---|---|---|---|---|---|---|---|---|
| | | ¹H NMR | | | | GPC[e] | | | |
| Polymer | Feed [LA]/[CL]/[OE] | [LA]/[CL]/[OE][a] | $\overline{Mn}$[b] | $W_{PEG}:W_{PLA/CL}$[c] | HLB[d] | $\overline{Mn}$ | $\overline{Mw}/\overline{Mn}$ | Yield % | Size[f] nm |
| MePEG$_{5000}$ | —/—/1 | —/—/1 | 5,000 | 100:0 | 20.0 | 4,350 | 1.1 | — | n.d. |
| PEG-b-PLA | 0.306/—/1 | 0.243/—/1 | 7,000 | 72:28 | 14.4 | 9,250 | 1.2 | 75 | 360 ± 40 |
| PEG-b-PCL | —/0.193/1 | —/0.166/1 | 7,150 | 70:30 | 14.0 | 8,900 | 1.3 | 85 | 470 ± 80 |
| PEG-b-PLACL | 0.169/0.086/1 | 0.100/0.068/1 | 6,700 | 75:25 | 15.0 | 10,000 | 1.2 | 80 | 370 ± 20 | n.d. not detected

[a] The [LA]/[CL]/[OE] molar ratio was determined from the integrations of the signals due to PLA blocks at 5.1 ppm, to PCL blocks at 4.0 ppm, and to PEG blocks at 3.6 ppm on the 1H NMR spectra
[b] $\overline{Mn} = \overline{Mn}_{PEG} + \overline{Mn}_{PLA/CL} = 5000 + 72 \times 5000/44 \times [LA]/[OE] + 114 \times 5000/44 \times [CL]/[OE]$
[c] $W_{PEG}:W_{PLA/CL} = \overline{Mn}_{PEG}:\overline{Mn}_{PLA/CL}$
[d] $HLB_{copolymer} = 20 \, (\overline{Mn}_{PEG}/\overline{Mn}_{copolymer})$
[e] Data obtained by GPC with respect to polystyrene standards from Polysciences.
[f] Polymer-stabilized ISA51 emulsion particles were determined by the particle size analyzer. Each value represents the mean of three experiments (mean ± s.d.)

The molar ratio of lactyl units to caproyl units to oxyethylene or [LA]:[CL]:[OE] was determined from the integrations of the proton resonances due to PLA blocks at 5.2 ppm, to PCL blocks at 4.1 ppm, and to PEG blocks at 3.6 ppm on the ¹H NMR spectra. The number average molecular weight ($\overline{Mn}$) were calculated according to the following equation:

$$\overline{Mn} = \overline{Mn}_{PEG} + \overline{Mn}_{PLA/CL} = 5000 + 72 \times 5000/44 \times [LA]/[OE] + 114 \times 5000/44 \times [CL]/[OE]$$

where 44, 72 and 114 are the molecular weights of OE, LA and CL repeat units, respectively. The HLB (hydrophilic-lipophilic balance) values of non-ionic copolymers PEG-b-

PLA, PEG-b-PCL, and PEG-b-PLACL were expressed according to Griffin's method as follows:

$$HLB_{copolymer} = 20\left(\frac{W_{PEG}}{W_{copolymer}}\right)$$

where $W_{PEG}/W_{copolymer}$ is the weight ratio of the hydrophilic portion of the main chain polymer and is obtained from $\overline{Mn}_{PEG}/\overline{Mn}_{copolymer}$. The most lipophilic polymer has an HLB number approaching 0, and the most hydrophilic polymer has a HLB of about 20. According to the equation, a high HLB value ($HLB_{PEG-b-PLA}$ of 14.4, $HLB_{PEG-b-PCL}$ of 14.0, and $HLB_{PEG-b-PLACL}$ of 15.0) was obtained, which indicated that the three copolymers had a high affinity to water.

The GPC traces of PEG-b-PLA. PEG-b-PCL, and PEG-b-PLACL exhibited monomodal and reflected rather narrow molecular weight distributions (Table 1), which indicated the absence of residual low molecular weight species. The $\overline{Mn}$ values calculated from GPC were higher than those from $^1$H-NMR. This finding could be attributed to changes in the hydrodynamic volume of the hydrophilic PEG and/or the lipophilic PLA, PCL, PLACL blocks as compared to the polystyrene standards.

Preparation of Polymer-Stabilized Emulsions

With the aim of enhancing the potency of emulsion-adjuvanted vaccines, we used hydrophilic PEG-b-PLA, PEG-b-PCL, and PEG-b-PLACL as emulsifiers to stabilize the interface between the ISA51 oily adjuvant and the antigen media. An aqueous phase of polymer dissolved in antigen media and an oily phase of ISA51 were emulsified using a homogenizer. The emulsifying formulation was perfectly white and isotropic from the top to the bottom.

Figure 1:
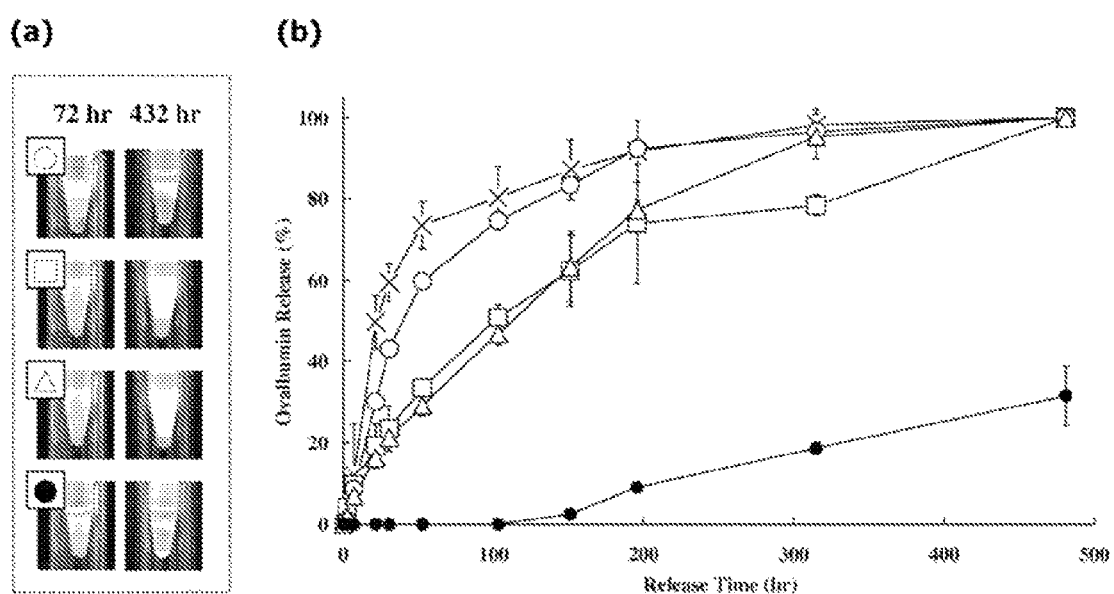
FIG. 1 shows (a) the visual aspects of emulsions stored at 37° C. and (b) the cumulative release of OVA from the emulsion formulations based on bioresorbable polymers and the oily adjuvant ISA51. (-x-) Non-formulation, (open circle) PEG-b-PLA/ISA51, (open square) PEG-b-PCL/ISA51, (open triangle) PEG-b-PLACL/ISA51, (filled circle) PBS/ISA51. The OVA-containing formulations (3 mg per 0.3 mL) were placed in a dialysis chamber in a centrifuge tube containing 2 ml PBS and stood at 37° C. The OVA release was regularly monitored by the BCA method (read by an UV-vis instrument at 562 nm, using calibration curves obtained from standard BSA solutions). The data are presented as the mean with standard deviation of three samples.

To mimic the usual storage conditions and the post-injection stage, the stability test was investigated at 4° C. and at 37° C. During the storage at 4° C., all emulsions were stable for a few weeks without phase separation. In the case of PEG-b-PLA/ISA51 and PEG-b-PCL ISA51, 10% of water disassociated after two weeks, but beyond this, no further water disassociation from the emulsion occurred. An isotropic emulsion could be re-formed by vortex mixing. On the other hand, approximately 10% of free oil at the surface layer disassociated from the PBS/ISA51 emulsion after one month under the same storage conditions. The PEG-b-PLACL/ISA51 emulsion was stable for at least six months without phase separation. During 60 days' monitoring at 37° C., the PEG-b-PCL/ISA51 and PEG-b-PLACL/ISA51 emulsions were stable without phase separation. On the other hand, approximately 10% of free oil at the surface layer disassociated from the PBS/ISA51 emulsion after 3 days (FIG. 1a). After one week, 30% of free oil at the surface and clear layers of water (30%) at the bottom disassociated from the emulsion. Phase separation happened at day 60, indicating the emulsion breaks. In the case of PEG-b-PLA/ISA51, the change in the visual aspect over time was similar to the PBS/ISA51.

Figure 2:
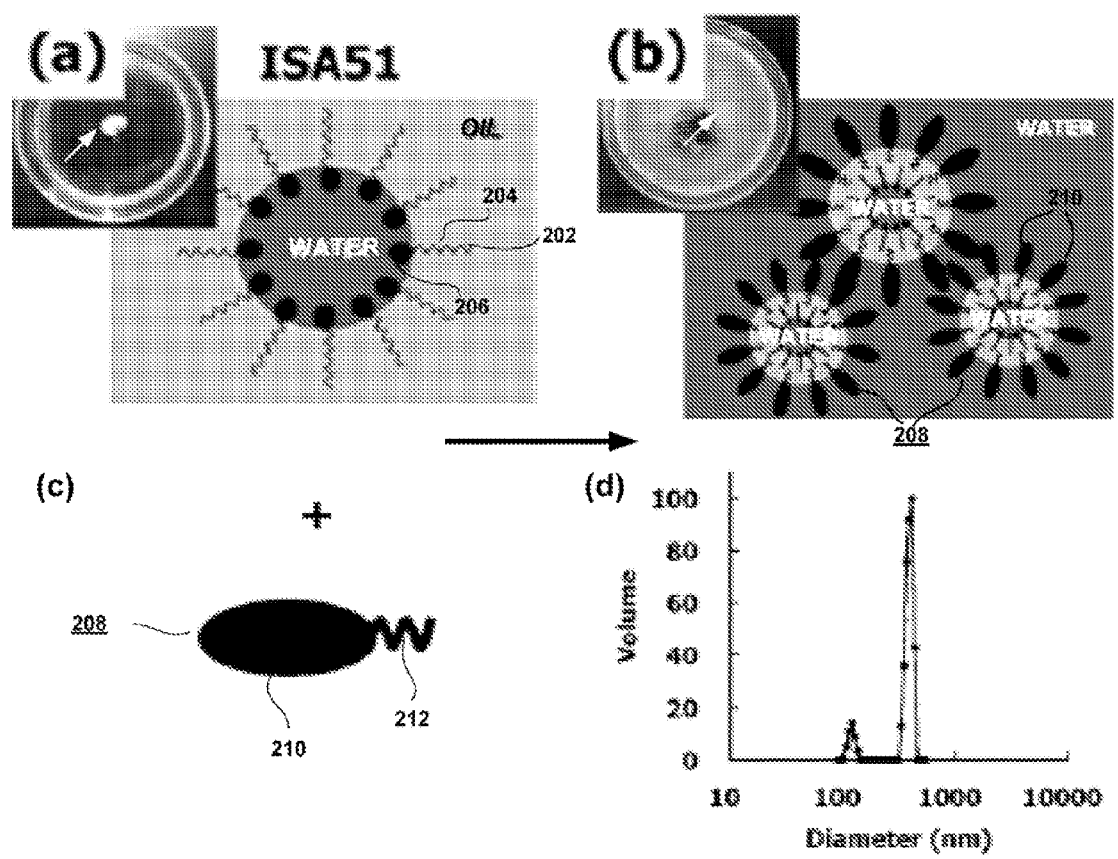
FIGS. 2(a)-2(d) are schematic presentations showing an ISA51-adjuvanted vaccine (a) before and (b) after stabilization with (c) a bioresorbable polymer. The ISA51 contains lipophilic mannide monooleate, which renders a W/O emulsion because of its high affinity for the oily phase. After incorporating the hydrophilic emulsifier PEG-b-PLA, PEG-b-PCL, or PEG-b-PLACL, in the antigen medium, the water affinity of the oily ISA51-adjuvanted vaccine was greatly enhanced so that the antigen-encapsulated stock emulsion was able to be re-dispersed in the PBS and resulted in an emulsion with homogeneous fine particles having (d) a particle size distribution of <1 μm.

The water affinity of the emulsions was investigated by the droplet test and laser light scattering. As shown in FIG. 2a, an emulsified PBS/ISA51 droplet (arrow in FIG. 2a inset) kept on floating on the water surface after 24 hr. The particle size was not detected by using light scattering technology. However, homogeneous particles with the size distribution of 1 μm were observed by optical microscope when re-dispersing the emulsion in the ISA51 oil solution (data not shown). On the other hand, each polymer-stabilized ISA51 droplet (arrow in FIG. 2b inset) could stand only for seconds in the aqueous phase and then diffuses in the water, which indicated its high affinity for water (FIG. 2b). The dynamic light scattering pattern showed that PEG-b-PLA, PEG-b-PCL or PEG-b-PLACL was a suitable emulsifier for the ISA51/water interface, and yielded narrowly distributed nanoparticles (FIG. 2d and Table 1). Typically, a bimodal distribution with two different sizes was observed, the relatively large particles of 500 nm and smaller ones of 100 nm (FIG. 2d). This dimension is appropriate for uptake by antigen-presenting cells (APCs) to facilitate the induction of potent immune responses due to the pseudo-natural targeting of antigens. Homogenization using MePEG failed to improve the water affinity of ISA51 emulsion. The droplet floated on the surface instead of diffusion in the water, which indicated that only PEG bearing short lipophilic units in the main chain polymer exhibited emulsifier property (FIG. 2c).

In addition to the water affinity, PEG-b-PLA-, PEG-b-PCL-, or PEG-b-PLACL-stabilized ISA51 emulsion also provided different controlled-release profiles to hydrophilic OVA protein with respect to free OVA or PBS/ISA51-formulated OVA, as shown in FIG. 1b. Initially, a fast release was observed in the case of OVA without formulation from which more than 50% of loaded OVA was released into the outside PBS medium within the first 30 hr. The PEG-b-PLA-modified ISA51 emulsion has similar release profiles to free OVA, in which less than 30% of OVA were released during the same period of time. Furthermore, the protein release increased continuously until it reached the equilibrium concentration in the inside and outside of the dialysis device. Conversely, the oily PBS/ISA51 emulsion presented well depot effect to OVA so that hydrophilic OVA was slowly released over 500 hr. Following the intermediate controlled-release mechanisms, the hydrophilic bioactive agents (or antigens) trapped within the PEG-b-PCL- or PEG-b-PLACL-stabilized emulsion will be released mostly by diffusion from the core oil to the surface, but also to a lesser extent by degradation mechanisms and emulsion breaks.

As shown in FIG. 2a, an ISA51 oily adjuvant contains only emulsifier of low HLB value (2.6 to mannide monooleate 202, in which the hydrophobic end 204 facing toward the oil phase, and the hydrophilic end 206 facing toward the aqueous phase). The water affinity test and in vitro release showed that the resulting PBS/ISA51 emulsion has a continuous phase of oil and the dispersed phase being water (FIG. 2a). On the other hand, a polymer-stabilized ISA51 system composes of two surfactants, hydrophilic polymer 208 and mannide monooleate 202, rendered a water-in-oil-in-water (W/O/W) multi-phase emulsion (FIG. 2b). In this case, oil droplets dispersed into the continuous water (stabilized by the polymeric emulsifier 208), and the core oil also entrapped an aqueous phase (stabilized by mannide monooleate 202; FIG. 2b). The polymer-emulsified particles could serve as either carriers or vehicles to deliver antigens to APCs in a targeted and prolonged manner.

From a viewpoint of emulsion stability, the vaccine emulsions met the requirements for in vitro storage and the post-injection depot. It is generally recognized that oil droplets with small particle size and homogeneous distribution are more stable. These parameters are however strongly influenced by the optimization of the emulsification process and the surfactant system. To this end, addition of excipients like glycine or glycylglycine in MONTANIDE® ISA 720, an oily adjuvant containing squalene and mannide monooleate, provided a potential way of stabilizing the emulsions during storage and post-injection. On the other hand, two O/W emulsion-type adjuvants that possess significant potential for the development of human vaccines are MF59® (developed from Novartis) and AS03 (developed from GlaxoSmithKline). MF59® is accomplished by using a combination of a hydrophilic-TWEEN® 80 emulsifier and a lipophilic SPAN® 85 (sorbitan trioleate), while AS03 is stabilized by TWEEN® 80 and alpha-tocopherol. In the present study, PEG-b-PLA-stabilized ISA51 emulsion remained the same or reduced the stability intrinsic to ISA51 oily adjuvant. However, homogenization of PEG-b-PCL- or PEG-b-PLACL-containing aqueous solution and the mannide monooleate-contained oily phase (e.g. ISA51) provides a potential way of stabilizing the emulsified particles both at storage and at post-injection stage conditions.

Immunological Evaluation in Mice

To further evaluate the potential applications of polymer-stabilized emulsions in vaccine adjuvants, the antibody assays were performed by subcutaneous vaccination in BALB/c mice with OVA, alone or formulated with PBS/ISA51 or PEG-b-PLACL/ISA51/PBS. The latter contained only 5% of ISA51 oily adjuvant in the formulation (See "MATERIALS AND METHODS" section: Immunization and ELISA immunoassay).

Figure 3:
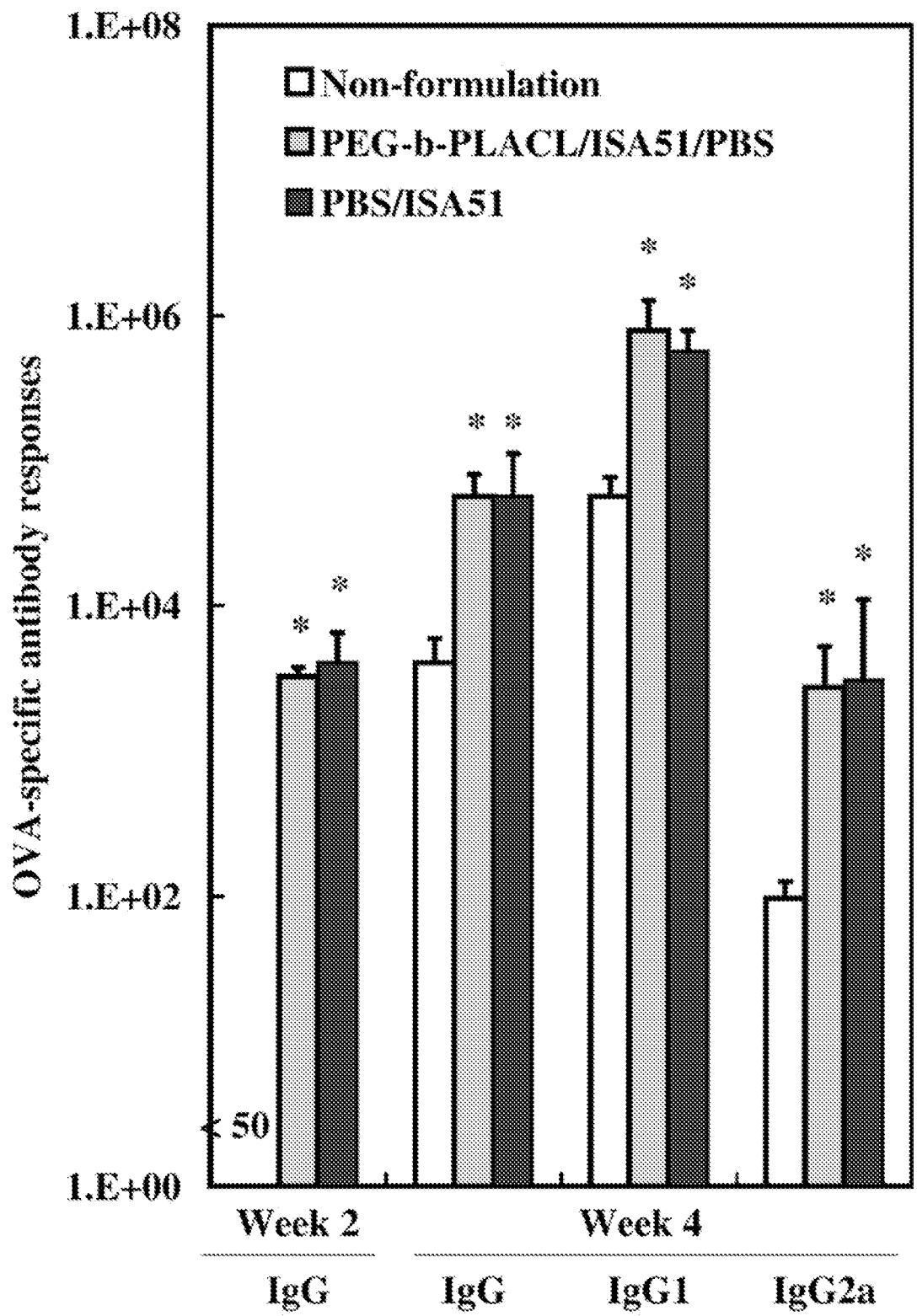
FIG. 3 is a graph showing specific antibody responses in mice following immunization with OVA in different formulations. BALB/c mice were subcutaneously vaccinated twice at weeks 0 and 2 with 0.5 μg of OVA. Sera were collected from blood and the antibody titers were measured by ELISA. The data are presented as geometric mean titers with standard errors (5 mice per group). *P<0.005: A comparison to the non-formulated OVA group was made at the same time point.

As shown in FIG. 3, the serum antibody IgG, IgG1 and IgG2a titers were significantly enhanced for the groups of PBS/ISA51- and PEG-b-PLACL/ISA51/PBS-formulated OVA in comparison with the group of OVA alone ($p<0.005$). Moreover, PEG-b-PLACL/ISA51/PBS-formulated OVA induced the same level of antibody titers as those induced by PBS/ISA51-formulated OVA. Thus, the PEG-b-PLACL/ISA51/PBS reserved the adjuvant effects of PBS/ISA51. We have attempted to study the effect of polymeric aqueous solutions on the enhancement of the OVA immunity. Our findings indicated that polymeric aqueous solutions had no adjuvant effect, the induced antigen (OVA)-specific antibodies were still at the same level as those without formulation (data not shown). We also observed that the PEG-b-PLACL/ISA51/PBS emulsion could be absorbed after 5 weeks of s.c. inoculation, while PBS/ISA51 emulsion still remained at the injection site. Furthermore, there was no adverse side effect in the animal.

After the injection, vaccine antigens may be directly taken up by APCs, bind to the surface antibody on B cells, or undergo degradation. Only those antigens that are taken by APCs can integrate into the immune responses. The pathway is largely dependent on the characteristics of the antigen, but may also be influenced by the presence of adjuvants. Although emulsion-type adjuvants have been widely used for several decades, their immunogenicity-enhancing effects are still controversial due to the lack of understanding about the complexity of colloidal dispersions, the emulsion stability of post-injection and the mechanism of the immune response. In the present study, the adjuvant effect of the W/O emulsion (PBS/ISA51 as an example) could be explained by the depot of emulsion that is capable of slowly releasing antigen over a long period of time. In the case of the W/O/W emulsion (PEG-b-PLACL/ISA51/PBS emulsion as an example), even with only 5% of ISA51 oily adjuvant, it induced significantly higher responses than non-formulated OVA. It is probable that W/O/W not only reserved the depot effects intrinsic to ISA51 oil, but also combined the antigen presentation effects. Moreover, the ameliorated W/O/W emulsion increases injectability and conceptually diminishes local reactions with respect to the W/O type vaccines produced from the same oil.

Amphiphilic copolymers consisting of 70 wt-% hydrophilic PEG block and 30 wt-% lipophilic PLA, PCL or PLACL block were synthesized by the ring-opening polymerization of lactide and/or e-caprolactone on monomethoxy $PEG_{5000}$. The resulting polymers can serve as a hydrophilic emulsifier to alter the water affinity of oily ISA51-adjuvanted vaccines so that the stock antigen-encapsulated emulsion could be re-dispersed into PBS before injection and thus resulting in stable and injectable W/O/W emulsion nanoparticles. Preliminary immunological evaluation showed that only 5% of oil within the PEG-b-PLACL/ISA51/PBS formulation reserves the adjuvant effects of the ISA51 oily adjuvant. These features are of great interest for further investigations of single-dose prophylactic and therapeutic vaccine development and via alternative immunization routes, such as intramuscular, transdermal or mucosal administration.

Example 2

The example here illustrates the synthesis and characterization of PEG-bearing PLA di- and triblock copolymers, PLA-PEG and PLA-PEG-PLA, prepared by the direct polycondensation of an aqueous lactic acid solution on monomethoxy or dihydroxyl PEG. Unlike the block copolymers reported in the literature, which were prepared in the presence of cytotoxic catalyst-containing heavy metals, in this study, no catalyst was added during polymerization, which increased the confident biocompatibility in the final material. The resulting copolymers ers were characterized by MALDI-TOF MS, GPC, and $^{1}H$-NMR. In contrast to micelles or nanospheres in which the polymer provides a matrix or a vehicle to encapsulate the bioactive agents, here we wanted to demonstrate whether the amphiphilic polymer could play an auxiliary role (as a surfactant) to stabilize the oil/water interface so that the bioactive candidates could be either surface attached or encapsulated within the core oil. The emulsifying properties were investigated by the homogenization of a polymer aqueous solution and oily squalene. Stability, size distribution, and in vitro release with ovalbumin (OVA) as model protein were performed to identify the resulting emulsion. For the sake of biocompatibility, squalene was selected as the core oil because it has a low toxicity and is used in the clinical trial (Siao et al., (2009) "Characterization and Emulsifying Properties of Block Copolymers Prepared from Lactic Acid and Poly(ethylene glycol)" *Journal of Applied Polymer Science* 114: 509-516, which is incorporated by reference in its entirety).

Polymer Synthesis

Lactic acid was purchased as a 85-90% aqueous solution from TEDIA (Fairfield, Ohio). Poly(ethylene glycol) 2000 monomethyl ether ($MePEG_{2000}$) and poly(ethylene glycol) 2000 ($diOH\text{-}PEG_{2000}$) were purchased from Fluka (Buchs, Switzerland). These materials were used without further purification. All solvents were analytical grade.

The PLA-PEG diblock copolymer was synthesized through the polycondensation of lactic acid on $MePEG_{2000}$, in the absence of any catalyst. Briefly, 10 g of $MePEG_{2000}$ and 10 g of an aqueous lactic acid solution were placed in a round-bottomed bottle. We performed the polymerization by distilling out water from lactic acid at 140° C. for 24 hr using a system composed of a Rotavapor® R-210 (Buchi Labortechnik AG, Switzerland) and vacuum pump V-700 (Buchi Labortechnik AG). The products were recovered by precipitation in an excessive amount of ethanol. They were further purified twice by successive dissolution/precipitation cycles with acetone as a solvent and ethanol as a nonsolvent to eliminate low-molecular-weight byproducts. The yield was about 25 wt-%. The PLA-PEG-PLA triblock copolymer was synthesized according to the same procedure with $diOH\text{-}PEG_{2000}$ used instead of $MePEG_{2000}$. The product was recovered by precipitation in cold ethanol (<10° C.), and the yield was about 30 wt %.

Measurements MALDI-TOF MS was recorded on a Waters® MALDI micro MX™ mass spectrometer (Milford, Mass.) equipped with a nitrogen laser (337 nm). All spectra were recorded in the reflection mode with an acceleration voltage of 12 kV. The irradiation targets were prepared from 0.1% trifluoroacetic acid (Riedel-de Haën, Seelze, Germany) in an acetonitrile/water mixture at a ratio of 50/50 (v/v) with α-cyano-4-hydroxy cinnamic acid (Sigma, Steinheim, Germany) as the matrix and sodium trifluoroacetate (Na-TFA, Fluka) as the dopant. The sample solutions were then spotted on a MALDI sample plate and air-dried before analysis. GPC was performed with a setup composed of an isocratic pump (Waters® high-performance liquid chromatography (HPLC) Model 510), a refractive index detector (Waters® 410 differential refractometer), and two columns connected in series, one PLgel 5-μm mixed-C column (100-Å pore size, 7.5×300 mm, Polymer Laboratories, Ltd., Shropshire, United Kingdom), and one PLgel 3-μm column 100-Å pore size, 7.5×300 mm). The mobile phase was tetrahydrofuran and the flow rate was 0.8 mL/min. Data were expressed with respect to polystyrene standards (Polysciences, Inc., Warrington, Pa.). $^1$H-NMR spectra were recorded at room temperature with a Varian VXR 300-MHz spectrometer (Varian, Palo Alto) with dimethyl sulfoxide-$d_6$ (Aldrich, Steinheim, Germany) and tetramethylsilane as the solvent and shift reference, respectively.

Polymer-Stabilized Emulsions

The polymer aqueous solution [120 mg of polymer dissolved in 0.8 mL of phosphate-buffered saline (PBS)] and 1.1 mL of squalene oil (Sigma, Steinheim, Germany) were emulsified with a Polytron® PT 3100 homogeniser (Kinematica AG, Lucerne, Switzerland) under 6000 rpm for 5 min. The emulsified formulations served as stocks for further physicochemical characterizations.

To mimic the usual storage conditions and the post-administration stage, the stability test was performed by placing each formulation at 4 and 37° C. and observed the visual aspects. To investigate the size distribution of the emulsions, the stock emulsion was redispersed in the PBS before the measurement by using the laser light-scattering technique with a Brookhaven 90 plus particle size analyzer (Brookhaven Instruments Limited, New York). In vitro release experiments were performed with the inverted dialysis tube method. Formulations containing OVA (albumin from chicken egg white, Grade V, Sigma; 3 mg/0.3 mL) were placed in a dialysis chamber (cutoff=0.2 μm, Pall Life Sciences, Ann Arbor, Mich.). The device was immersed in a 50-mL centrifuge tube containing 2 mL of PBS and left to stand at 37° C. At different time intervals, 100 μL of sample were aspirated from the medium outside of the chamber and replaced with 100 μL of fresh PBS buffer. The OVA release was regularly determined by the bicinchonic acid method (BCA™ protein assay kit, Pierce. Rockford, Ill.).

Results and Discussion

Figure 4:
FIGS. 4(a)-4(b) show the schemes for synthesizing (a) the diblock copolymer PLA-PEG and (b) the triblock copolymer PLA-PEG-PLA.
Figure 4:
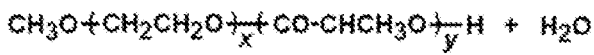
Figure 4:
Figure 4:
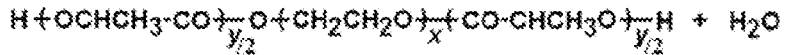

FIG. 4 shows the synthesis and the chemical structure of the block copolymers. The PLA-PEG diblock copolymer was synthesized by the polycondensation of lactic acid in the presence of monomethoxy PEG, which resulted in a copolymer composed of a hydrophilic block PEG and a lipophilic block PLA. Similarly, the triblock copolymer PLA-PEG-PLA was obtained from the polymerization of lactic acid in the presence of dihydroxyl PEG. In general, PLA compounds are synthesized by the ring-opening polymerization of lactide (a cyclic diester of lactic acid) or the polycondensation of lactic acid. Although the latter is a reasonably low-cost and straightforward method for synthesizing polymers bearing PLA segments, this route generally leads to oligomers with low-molar-mass chains. The molecular characteristics of the resulting copolymers are summarized in Table 2.

Characterization of the PLA/PEG Block Copolymers by MALDI-TOF MS

Figure 5:
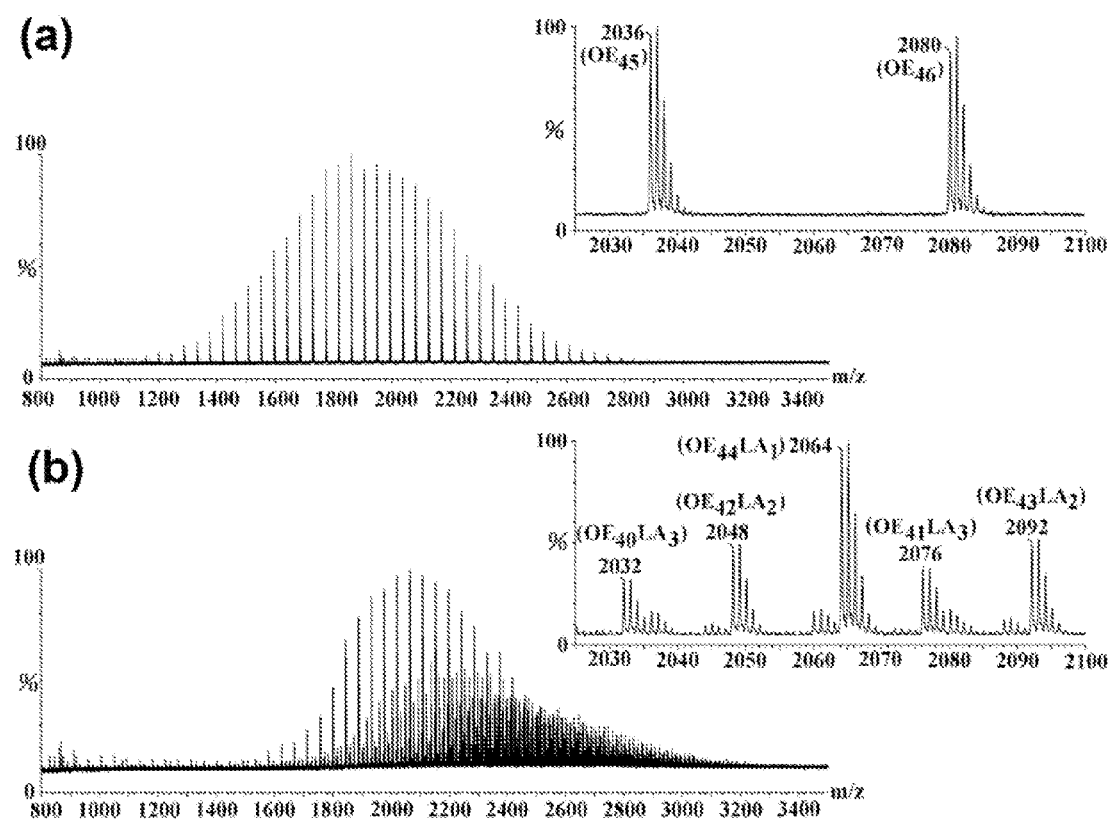
FIGS. 5(a)-5(b) show the MALDI-TOF mass spectra of (a) MePEG$_{2000}$ and (b) PLA-PEG.

Mass spectrometry is used to measure the real MW of synthetic polymers. With this technique, the molecular structure and chemical composition of copolymers can be accurately studied. FIGS. 5a-5b show the MALDI-TOF MS spectra of PLA-PEG and the corresponding MePEG$_{2000}$. The MePEG$_{2000}$ spectrum was well resolved [FIG. 5(a)], and the peaks were separated by 44 mass units, which corresponded to the MW of the PEG monomer (oxyethylene (OE) units=44.03 g/mol). The subsidiary peaks were assigned to the isotopes of elements. The MW of MePEG$_{2000}$ ranged from 1200 to 2800 g/mol with Mn=1970 and Mw/Mn=1.05. After the condensation (140° C. 24 h, no catalyst) of the lactic acid aqueous solution in the presence of MePEG$_{2000}$, the MW distribution of the resulting polymer shifted to 1600-3200 g/mol with Mn of 2370 and Mw/Mn=1.03 [FIG. 5b], which indicated the chain extension of the lactyl (LA) monomer onto the macroinitiator MePEG. No signals characteristic of MePEG were detected on the MALDI-TOF MS spectra of PLA-PEG, which indicated that PLA-free MePEG$_{2000}$ species were removed during purification. On the spectra of MePEG$_{2000}$ and PLA-PEG, the number of oxyethylene units (OE) and lactyl (LA) units could be uniquely determined (x and y, respectively) from the MW of the major peaks. Each major peak in the mass spectrum corresponded to a polymer species (molecular structure proposed in FIG. 4) that has OE units and LA units (MW=72.06) in addition to the end groups (one methyl and one hydroxyl, MW=32.03) and a Na$^+$ ion (MW=22.99, due to Na-TFA).

$$MW_{MePEG} = x(44.03) + 32.03 + 22.99$$

$$MW_{PLA-PEG} = x(44.03) + y(72.06) + 32.03 + 22.99$$

For example, the major five polymer species between 2030 and 2100 m/z in the spectra of PLA-PEG (FIG. 5b) are represented as follows:

$$MW_{PLA-PEG} = 2032, x=40, y=3$$

$$MW_{PLA-PEG} = 2048, x=42, y=2$$

$$MW_{PLA-PEG} = 2064, x=44, y=1$$

$$MW_{PLA-PEG} = 2076, x=41, y=3$$

$$MW_{PLA-PEG} = 2092, x=43, y=2$$

Figure 6:
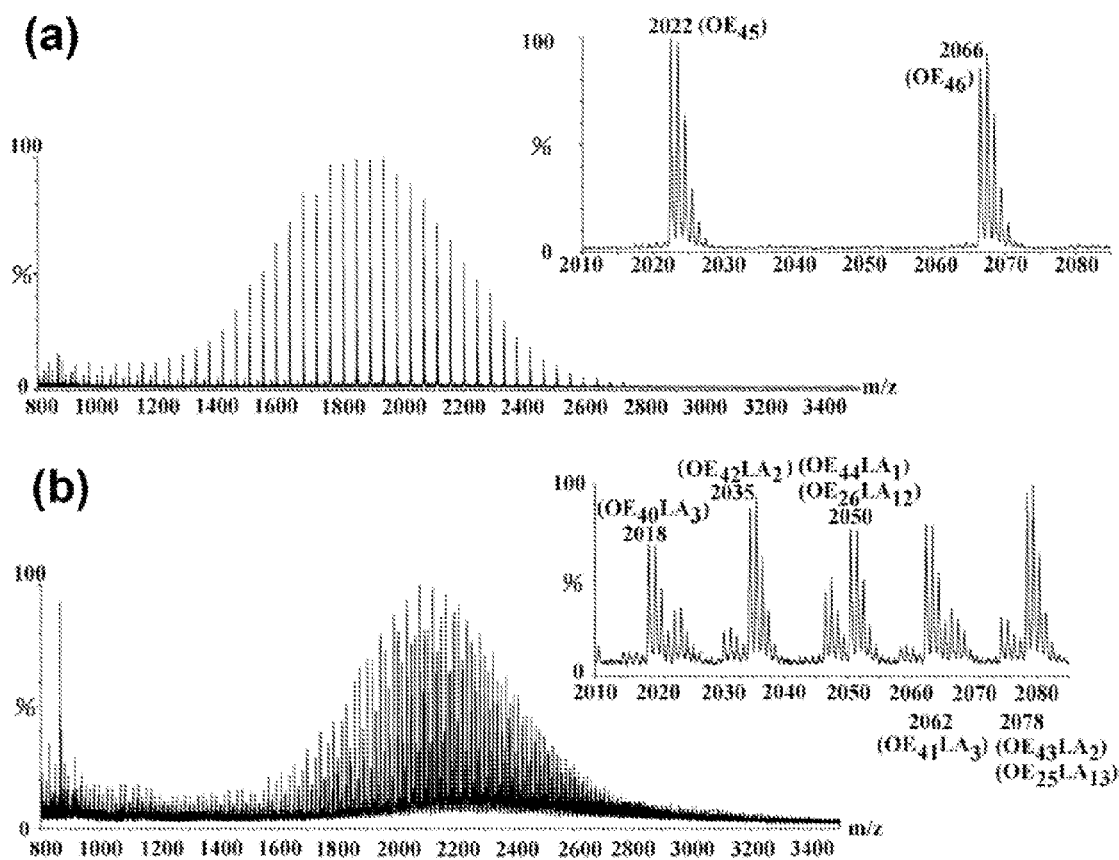
FIGS. 6(a)-6(b) show the MALDI-TOF mass spectra of (a) diOH-PEG$_{2000}$ and (b) PLA-PEG-PLA.

To substantiate the speculation of correlation between the MW and molecular architecture of copolymers, the same method can be employed for the analysis of the triblock copolymer PLA-PEG-PLA. Each major peak in the mass spectrum, as shown in FIG. 6, corresponded to a polymer species that had OE units. LA units, the end groups of one hydrogen and one hydroxyl, and Na$^+$ ion:

$$MW_{diOH-PEG2000} = x(44.03) + 18.02 + 22.99$$

$$MW_{PLA-PEG-PLA} = x(44.03) + y(72.06) + 18.02 + 22.99$$

For example, the major five polymer species between 2010 and 2080 m/z in the spectra of PLA-PEG-PLA (FIG. 6b) were represented as follows:

$$MW_{PLA-PEG-PLA} = 2018, x=40, y=3$$

$$MW_{PLA-PEG-PLA} = 2035, x=42, y=2$$

$MW_{PLA-PEG-PLA}=2050, x=44, y=1$ or $x=26, y=12$ $MW_{PLA-PEG-PLA}=2062, x=41, y=3$ $MW_{PLA-PEG-PLA}=2078, x=43, y=2$ or $x=25, y=13$

After calculating the repeat unit masses and the end group masses through the MALDI spectra, we could distinguish the molecular structure between the diblock and triblock copolymers. The hydrophilic-lipophilic balance (HLB) value of the nonionic PLA/PEG diblock or triblock copolymer was expressed according to Griffin's method as follows:

$$HLB_{PLA/PEG}=20\times(W_{PEG}/W_{PLA/PEG})$$

where $W_{PEG}/W_{PLA/PEG}$ is the weight ratio of the hydrophilic portion of the main-chain polymer and was obtained from $Mn_{PEG}/Mn_{PLA/PEG}$. The most lipophilic portion has an HLB number approaching 0, and the most hydrophilic portion has a number of about 20. According to this equation, high HLB values ($HLB_{PLA-PEG}=16.6$ and $HLB_{PLA-PEG-PLA}=16.4$) were obtained, which indicated that the two copolymers had high affinities for water. There was however no significant difference between the copolymers initiated by $MePEG_{2000}$ and the copolymers initiated by $diOH-PEG_{2000}$.

TABLE 2

| Polymer | MALDI-TOF MS[a] | | GPC[b] | | ¹H NMR[c] |
|---|---|---|---|---|---|
| | Mn | Mw/Mn | Mn | Mw/Mn | Mn |
| MePEG$_{2000}$ | 1970 | 1.05 | 2650 | 1.10 | 2000 |
| PLA-PEG | 2370 | 1.03 | 3360 | 1.08 | 2150 |
| diOH-PEG$_{2000}$ | 1840 | 1.04 | 2700 | 1.08 | 2000 |
| PLA-PEG-PLA | 2240 | 1.04 | 3520 | 1.07 | 2200 |

[a]Data obtained by MALDI-TOF MS with α-cyano-4-hydroxy cinnamic acid as the matrix and Na-TFA as a dopant.
[b]Data obtained by GPC with respect to polystyrene standards from Polysciences.
[c]Mn = Mn$_{PEG}$ + Mn$_{PLA}$ = 2000 + 72 × 2000/44 × ([LA]/[OE]), where [LA]/[OE] was determined from the integrations of the signals due to the PEG blocks at 3.6 ppm and to the PLA blocks at 1.5 ppm on the ¹H NMR spectra.

MW Determined by GPC and ¹H-NMR

GPC is a separation technique based on the molecular hydrodynamic volume. By comparing with a standard curve of a known MW species, the relative MW of the samples could be easily calculated. Table 2 shows molecular characteristics of the block copolymers of PEG and lactic acid initiated by PEG. The average MW increased after the introduction of lactic acid chains onto the prepolymer PEG. The GPC traces of PLA-PEG and PLA-PEG-PLA exhibited monomodal distributions and reflected rather narrow MW distributions, which indicated the absence of residual low-molecular-weight species. ¹H-NMR data revealed that these low-molecular-weight species consisted of unreacted lactic acid and/or LA-rich species. The Mn values calculated from GPC were higher than those calculated from MALDI-TOF MS and ¹H-NMR (Table 2). This finding could be assigned to changes in the hydrodynamic volume of the hydrophilic PEG and/or PLA blocks as compared with that of the polystyrene standards.

The LA units/OE units molar ratio or [LA]/[OE] was determined from the integrations of the proton resonances due to PEG blocks at 3.6 ppm and to PLA blocks at 1.5 ppm on the ¹H-NMR spectra. The single peak at 3.3 ppm assigned to the hydrogens of methyl groups was also detected on the NMR spectra of MePEG$_{2000}$ and PLA-PEG. The MW of the copolymers was determined according to the followings relationship:

$$\overline{M}_n(NMR) = \overline{M}_{n_{PEG}} + \overline{M}_{n_{PLA}}$$
$$= 2000 + 72 \times 2000/44 \times ([LA]/[OE])$$

where 44 and 72 were the MWs of the OE and LA repeat units, respectively, and 2000 was the average MW of PEG indicated by the supplier.

Emulsifying Properties of Amphiphilic Block Copolymers

To demonstrate whether PLA-PEG and PLA-PEG-PLA could be used as emulsifiers, the polymer aqueous solution was homogenized with squalene oil, which resulted in an isotropic emulsified formulation. The emulsions remained stable for a few weeks when they were stored at 4° C. After 2 weeks, 5% of water disassociated, but beyond this no further water disassociation from the emulsion occurred. The isotropic emulsion could be reformed by vortex mixing. Little difference was observed between the PLA-PEG- and PLA-PEG-PLA-stabilized emulsions. Homogenization of squalene oil with MePEG$_{2000}$ or diOH-PEG$_{2000}$ failed to stabilize the squalene/water interface. This indicated that even bearing only short PLA units in the main-chain polymer PLA-PEG or PLA-PEG-PLA, the block copolymer could display an amphiphilic behavior.

Figure 7:
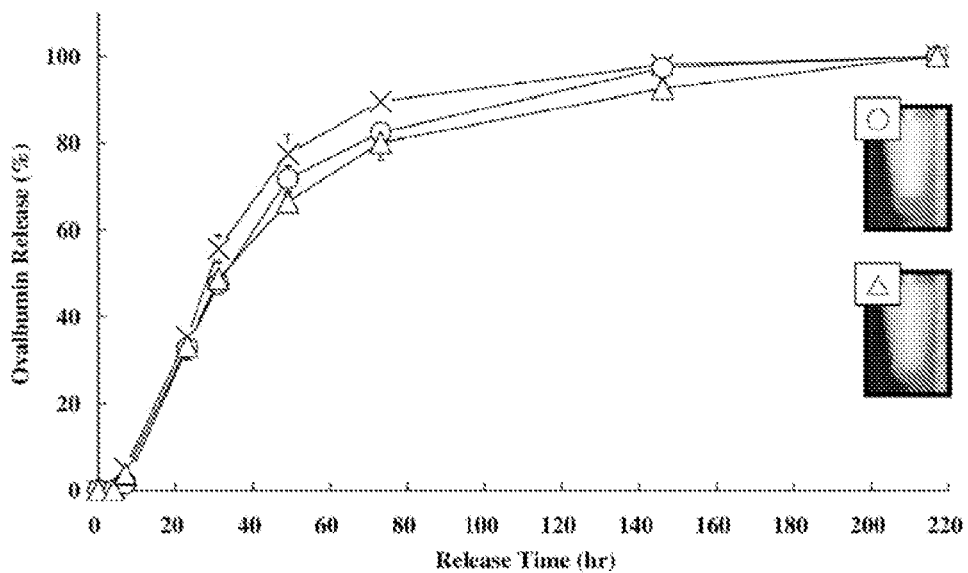
FIG. 7 is a graph showing the in vitro OVA release from the squalene emulsions based on the PLA-PEG and PLA-PEG-PLA. The OVA-containing formulations (3 mg per 0.3 mL) were placed in a dialysis chamber in a centrifuge tube containing 2 ml of PBS and stood at 37° C. The release was regularly monitored by the BCA method and read by an UV-vis instrument at 562 nm using calibration curves obtained from standard BSA solutions. Data are presented as the mean with standard errors of three samples. (-x-) Non-formulation, (open circle) PLA-PEG/squalene, (open triangle) PLA-PEG-PLA/squalene.

The size distribution of the emulsions and in vitro OVA release were measured to identify the dispersion characteristics of the resulted emulsions and to understand the effect of the copolymer in the emulsification process. The emulsion was redispersed in the PBS and the size distribution was measured with a particle size analyser. Typically, a water-in-oil (W/O) emulsion droplet remains floating on a water surface, and the particle size is undetectable with a light-scattering technology. Conversely, an O/W emulsion droplet can stand only for seconds in an aqueous phase and then diffuses into the water. The dynamic light-scattering pattern showed that PLA-PEG or PLA-PEG-PLA was a suitable emulsifier for squalene/water emulsions and yielded narrowly distributed nanoparticles in the PBS. Table 3 shows physicochemical characteristics of the squalene emulsions based on PLA-PEG and PLA-PEG-PLA, FIG. 7 shows the cumulative release of OVA from different formulations. Initially, a fast release was observed in the nonformulated OVA, from which more than 80% of loaded OVA were released into the outside PBS medium within the first 50 hr. The PLA-PEG/squalene or PLA-PEG-PLA/squalene emulsion allowed a slight delay, then the protein was quickly released. The visual aspect showed that the emulsions remained stable, only 5% of water disassociated at the bottom over 200 h at 37° C. Surfactants as emulsifiers can be defined by their HLB values, which give information about the relative affinity to aqueous and oily phases. A lipophilic emulsifier renders a W/O emulsion with a high affinity to an oily phase, whereas a hydrophilic emulsifier renders an O/W emulsion with a high affinity to an aqueous phase. These are however strongly influenced by the optimization of the surfactant system and the emulsification process. Here, light-scattering and in vitro release data indicated that polymers with high HLB values rendered a stable O/W emulsion. Moreover, no significant difference was found between PLA-PEG- and PLA-PEG-PLA-stabilized emulsions.

TABLE 3

| Component | | | Emulsion | Particle |
|---|---|---|---|---|
| Aqueous phase | Oily phase | HLB[a] | type | size (nm)[b] |
| PLA-PEG/PBS | Squalene | 16.6 | O/W | 343 ± 67 |
| PLA-PEG-PLA/PBS | Squalene | 16.4 | O/W | 331 ± 68 |

[a] $HLB_{PLA/PEG} = 20\,(\overline{M}_{n\,PEG}/\overline{M}_{n\,PLA/PEG})$.
[b] Each value represents the mean of three experiments (Mean ± Standard deviation).

Mostly, degradable aliphatic polyesters used for vaccine or protein delivery have been in the form of injectable microspheres or implant systems. Such systems require complicated fabrication processes using organic solvents, which may cause denaturation when antigens (virus or proteins) are to be encapsulated. Moreover, the systems require polymers with high MW (generally >50,000 Da), which require severe polymerization conditions (extreme temperature and pressure and toxic catalysts). In this study, the stable squalene/water emulsions were obtained with PEG-containing PLA oligomers as emulsifiers without the addition of any other stabilizer. The bioactive candidates could be either surface attached to or encapsulated within a core oil. The obtained emulsions had a high affinity to water so that nanoparticles were obtained after they were redispersed into the PBS. Moreover, no catalyst was required for the preparation of the designed polymers. The emulsified formulation developed here was free of organic solvents. These features are of great interest for a local delivery of bioactive agents, especially for applications in candidate vaccines delivery and anti-cancer treatments.

Conclusion

PLA/PEG diblock and triblock copolymers with high HLB values were synthesized by the direct polycondensation of an aqueous lactic acid solution on monomethoxy PEG or dihydroxyl PEG in the absence of a catalyst. MALDI-TOF MS data allowed us to calculate the repeat unit masses and end-group masses so that the molecular structure between the diblock and triblock copolymers could be distinguished. The obtained copolymers could serve as hydrophilic emulsifiers and rendered stable O/W emulsified nanoparticles when the polymer aqueous solution was homogenized with squalene oil. Little difference was found in the physiochemical characteristics, such as the stability, particle size, and emulsion type between the PLA-PEG- and PLA-PEG-PLA-stabilized emulsions. These formulations have potential to be used in a delivery system for prophylactic and therapeutic vaccine candidates and for anticancer drugs.

Example 3

This example illustrates the use of an amphiphilic polymer, namely, poly(ethylene glycol)-block-poly(lactide-co-ε-caprolactone) (PEG-b-PLACL), as an emulsification agent to render different types of vaccine formulations. The hydrophilic block was made of PEG because of its availability, water-solubility, and high biocompatibility. Degradable aliphatic polyesters, in particular polylactides (PLA) and poly(ε-caprolactone) (PCL), have been widely used as medical and drug delivery devices with FDA approval. PLA with variable chain stereoregularity provides a worthwhile means to adjust the rate of degradation, in addition to its physical and mechanical properties. The degradation products of PCL have a relatively higher pKa than those of poly(lactide-co-glycolide) (PLG) (4.8 for ε-hydroxycaproic acid, and 3.8 for lactic acid and glycolic acid at 25° C.), and they may provide more conservation of protein molecular integrity when being used for a long-term controlled delivery of proteins. PLACL was thus chosen as a lipophilic block for its fast degradation characteristics. In addition, its amorphous nature provides good affinity between the polymer matrix and oil solutions. Squalene was selected as the core oil because unlike mineral oil, it is natural and metabolizable. The excipient use of SPAN® 85 in the oily phase is also positively indicated, as it is an emulsifying agent in licensed human vaccines. Various properties of emulsions have been characterized, including stability, the droplet test, microscopic aspects, and the in vitro release profile of a model antigen ovalbumin (OVA). The B-cell and T-cell responses in mice after immunization were characterized to evaluate the immunogenicity-enhancing effect of novel emulsion-type vaccine formulations (Huang et al., (2009) "Formulation and Immunological Evaluation of Novel Vaccine Delivery Systems Based on Bioresorbable Poly(ethylene glycol)-block-poly(lactide-co-ε-caprolactone" *J Biomed Mater Res Part B: Appl Biomater* 90B: 832-841, which is herein incorporated by reference in its entirety).

Materials and Methods

Polymer Synthesis and Characterization

PEG-b-PLACL was synthesized by the ring-opening polymerization of lactide (Aldrich) and ε-caprolactone (CL. Aldrich), using $SnOct_2$ (stannous octoate, Sigma) as a catalyst and MePEG (polyethylene glycol 5000 monomethyl ether, Fluka) as an initiator. Briefly, predetermined amounts of MePEG (2.1 g), lactide (0.58 g), and ε-caprolactone (0.47 g) were placed in a dried round-bottomed bottle, and the appropriate amount of $SnOct_2$ (30 mg) was added as a solution in dried toluene (10 mL). The polymerization was performed at 140° C. under reflux for 24 h. The product was recovered by precipitation in an excessive amount of ethanol. The yield was ~75 wt %. The resulted polymer was characterized by $^1H$ nuclear magnetic resonance ($^1H$ NMR) and gel permeation chromatography (GPC). $^1H$ NMR spectra, were recorded at room temperature with a Varian VXR 300 MHz spectrometer (Varian, Palo Alto) using deuterated chloroform as a solvent. The molar ratio of oxyethylene to lactyl units to caproyl units or [OE]:[LA]:[CL] was determined from the integrations of the proton resonances due to PEG blocks at 3.6 ppm, to PLA blocks at 5.2 ppm and to PCL blocks at 4.1 ppm on the $^1H$ NMR spectra. The average molecular weights ($\overline{M}_n$) were calculated on the basis of the $\overline{M}_n$ of PEG ($\overline{M}_n$=5000 daltons) according to the following equations:

$$\overline{M}_{n\,PEG\text{-}b\text{-}PLACL}=5000+72\times5000/44\times[LA]/[OE]+114\times5000/44\times[CL]/[OE]$$

where 44, 72, and 114 are the molecular weights of OE, LA, and CL repeat units, respectively. The hydrophilic-lipophilic balance (HLB) value of nonionic PEG-b-PLACL is expressed according to the Griffin's method as follows:

$$HLB_{PEG\text{-}b\text{-}PLACL}=20(W_{PEG}/W_{PEG\text{-}b\text{-}PLACL})$$

where $W_{PEG}/W_{PLA/PEG}$ is the weight ratio of the hydrophilic portion of the main chain polymer and is obtained from $M_{n\,PEG}/\overline{M}_{n\,PEG\text{-}b\text{-}PLACL}$.

GPC was performed by using a setting composed of a Waters 510 HPLC pump, a Waters 410 differential refractometer, one PLgel mixed-C 5 μm 100 Å column (7.5×300 mm), and one PLgel 3 μm 100 Å column (7.5×300 nm n), and the mobile phase being THF and the flow rate being 0.8 mL/min. Data were expressed with respect to polystyrene standards from Polysciences. A unimodal and narrow molecular weight distribution (polydispersity index being 1.1) was observed in GPC chromatograms of PEG-b-PLACL and the corresponding $MePEG_{5000}$, which indicated a full initiation of the macroinitiator.

The fact that the polymer PEG-b-PLACL aqueous solution forms micelles is an indication that the polymer possesses an amphiphilic nature. This was confirmed by dye solubility experiments and light scattering analysis. Briefly, five milligrams of polymer were added to 1 ml of PBS in the presence of the water-insoluble dye diphenylhexatriene (DPH, SIGMA™), which is known to dissolve in the hydrophobic core of polymeric micelles or aggregates. After sonication and centrifugation, an abrupt enhancement in the ultraviolet (356 nm) absorption of the dye was observed, which was an indication of micelle formation. The particle size distribution was determined by using the laser light scattering technique with a Brookhaven 90 plus particle sizer (Brookhaven. Instruments Limited).

Polymer-Based Emulsions

An aqueous solution containing PEG-b-PLACL (120 mg) dissolving in an antigen medium (OVA in 0.8 mL of PBS) and 10.1 mL of an oily phase containing squalene only or squalene/SPAN® 85 mixture (85/15 v/v) were emulsified with a POLYTRON® PT 3100 homogenizer (Kinematica AG, Swiss) at 6000 rpm for 5 min. A polymeric surfactant-free emulsion composed PBS/SQUALENE/SPAN® 85 was also prepared at 8000 rpm for 10 min. These emulsified formulations serving as stocks for further physicochemical characterizations, including stability, the droplet test, microscopic aspects, and in vitro release. The stability test was performed by placing each formulation at 4° C. and observed the emulsion at predetermined time points (2 weeks, 1 month, 3 months, 6 months, 1 year). The droplet test was assessed by placing a droplet (20 μL) of emulsion into a water-containing beaker (200 mL). The microscopic aspects of the emulsions were investigated by redispersing them (100 μL) into a continuous phase (900 μL) and monitoring with an Olympus DP70 microscope. Particle size distribution was determined by using the laser light scattering technique. The In vitro release experiments were performed by using the inverted dialysis tube method. OVA-containing formulations (3 mg per 0.3 mL) were placed in a dialysis chamber (cutoff 0.2 μm) and the device was then immersed in a 50 mL centrifuge tube containing 2-mL of PBS at 37° C. At different time points, 100 μl of sample were aspirated from the medium outside of the chamber and replaced with 100 μL of fresh PBS buffer. The OVA release was regularly determined by the bicinchonic acid method (BCA™ protein assay kit. Pierce).

Mice and Immunizations

Five-week old female BALB/c mice were obtained from the National Laboratory Animal Breeding and Research Center (Taipei, Taiwan) and acclimatized for at least 1 week at the animal facility of the National Health Research Institutes (NHRI, Miaoli, Taiwan) before use. All animal studies were approved by the Animal Committee of the NHRI. Mice were immunized subcutaneously with syringe needles of 27G×½" at weeks 0, 2, and 4 by 0.5 μg of OVA in PBS or formulated with PEG-b-PLACL/squalene or PEG-b-PLACL/squalene/SPAN® 85 or aluminum phosphate suspension (alum, 150 μg per dose). To increase the fluidity, the PEG-b-PLACL/squalene and PEG-b-PLACL/squalene/SPAN® 85 formulations were prepared by redispersing 100 μL of a stock emulsion (see MATERIALS AND METHODS: Polymer-Based Emulsions) into 900 μL of PBS before the injections, which resulted in the formulations with ~5% oil. Sera and spleen collections were performed to determine B- and T-cell responses, respectively.

IgG and Its Isotypes in Immunity

To determine the B-cell response, mice were bled at the lateral tail vein and the collected sera were stored at −30° C. until assaying. The presence of OVA-specific antibodies in the sera was determined by enzyme-linked immunosorbent assay (ELISA). In brief, 100 μL of diluted OVA (10 μg/mL) were coated onto 96-well microtiter plates with 0.05M carbonate buffer (pH 9.6) for overnight incubation at 4° C. The coated plates were washed twice with PBS containing 0.05% TWEEN® 20 (SIGMA™) and then blocked with 5% nonfat milk in PBS at room temperature for 2 h. Diluted sera (starting dilution 1:50, serial threefold serum dilutions) from immunized animals were applied to wells at room temperature for 2 h. After the addition of HRP-conjugated goat anti-mouse IgG (ICN Cappel), the assay was developed with the substrate solution tetramethylbenzidine (TMB, SURE BLUE™, KPL) and the reaction was stopped with 2N $H_2SO_4$. Plates were read at 450 nm using an ELISA plate reader (Molecular Devices, Sunnyvale, Calif.). The data for each sample were fit using a curve-fitting method to an exponential function, and the titers were expressed as the reciprocal dilution that gave an optical density of twofold absorbance of preimmune sera. For isotype determination, 100 μL of an appropriate dilution (1:2000) of HRP-rabbit anti-mouse IgG1 (ZYMED®, CA) or HRP-rabbit anti-mouse IgG2a (ZYMED®, CA) was added. The statistical significance ($p<0.05$) was determined by performing a two-tailed Student's t-test on log-transformed values.

T-Cell Immune Responses

To determine T-cell responses, 1 week after the boost, the mouse spleen was removed aseptically and placed in an eppendorf containing 1 mL of culture medium (cRPMI) consisting of RPMI 1640 (SAFC, Kansas) with 2 mM L-glutamine, and supplemented with 25 mM HEPES (Gibco, invitrogen, NY), 0.05 mM 2-mercaptoethanol, 10% heat inactivated fetal bovine serum (FBS, HyClone, Perbio) and 1% antibiotics. The single cell suspension was prepared using the end of a syringe and grinding the spleen through a cell strainer (BD, Biosciences). The cell suspension was collected in a 50 mL centrifuge tube and then centrifuged at 1000 rpm for 5 min. To remove the erythrocytes, the cell pellet was resuspended in 5 mL of the ACK lysis buffer, placed to room temperature for 1 min, terminated the reaction with 20 mL RPMI 1640, followed by centrifugation for 5 min. The pellet was washed twice with cRPMI and resuspended in 5-mL of cRPMI. After cell counting with a hemocytometer using the trypan blue dye exclusion technique, U-bottomed 96-well plates were seeded with $2 \times 10^5$ cells in cRPMI at a total volume of 200 μL per well. Cells were stimulated in triplicate in the presence or absence of 10 μg/mL of OVA. Concanavalin A (Con A, 5 μg/mL, SIGMA™)) was used as a positive control, and plates were then incubated for 5 days at 37° C. in 5% $CO_2$ in humidified air. Cellular proliferation was assessed by the addition of 1 μCi of tritiated methylthymidine (Perkin Elmer, Mass.) to the cell suspension for the final 16 h of culture. Interferon-γ (IFN-γ) and interleukin-4 (IL-4) concentrations in supernatants were measured by ELISA using paired antibodies according to the manufacturer's instructions (R&D Systems, Abingdom).

Results

Polymer Design and Polymer-Based Emulsions

A diblock copolymer consisting of 75 wt % of the hydrophilic block PEG and 25 wt % of the lipophilic block PLACL with molecular weight of 7000 daltons, polydispersity index of 1.1 and a calculated HLB of 15 was synthesized via the ring-opening polymerization of lactide and ε-caprolactone on monomethoxy PEG with the catalyst $SnOct_2$. The amphiphilic nature of PEG-b-PLACL was confirmed by self-association of micelles in the polymer aqueous solution. Dynamic light scattering displayed polymeric micelles with a unimodal size distribution with an average diameter of 18.20±0.4 nm. Preliminary immunogenicity studies however showed that the polymeric aqueous solution had no adjuvant effect because they induced the same level of antigen (OVA)-specific antibodies as those formulations without the adjuvant (data not shown).

With the aim of enhancing the vaccine potency, the amphiphilic polymer was used as an emulsifier to make different emulsion-type formulations by homogenizing a mixture of the polymer aqueous solution and squalene or the squalene/SPAN® 85 oil (FIG. 8a). Table 4 lists the physicochemical characteristics of various formulations based on the bioresorbable polymer PEG-b-PLACL and selected oils. The emulsified formulation was white and isotropic from the top to the bottom (FIG. 8b). FIG. 8c shows the stability of the emulsions stored at 4° C. The emulsion PEG-b-PLACL/squalene/SPAN® 85 was stable for at least 1 year without occurrence of phase separation. Conversely, ~10% of free oil at the surface layer disassociated from the emulsion-PBS/squalene/SPAN® 85 after 1 month. In the case of the emulsion PEG-b-PLACL/squalene with aqueous/oily being 5/5 w/w, 20% of water disassociated under the same storage conditions after 2 weeks, but beyond this no further water disassociation from the emulsion occurred. An isotropic emulsion could be reformed by homogenization in the same condition or simply by vortex mixing. An increase in the squalene content could significantly enhance the stability of the emulsion PEG-b-PLACL/squalene and result in a stable emulsion without phase separation for at least 1 year when the aqueous/oily was 3/7 w/w.

The type of dispersion of the emulsion was examined by a droplet test, microscopic aspects, and in vitro release. The droplet test allowed the identification of a continuous phase of emulsion. A droplet of PBS/squalene/SPAN® 85 emulsion remained floating on the water surface after 24 h (FIG. 9a) even after gentle hand stirring of the beaker. Conversely, the PEG-b-PLACL/squalene emulsion droplet could stand for only one half-hour in an aqueous phase and then diffused into the water (FIG. 9b), a feature similar to the PEG-b-PLACL/squalene/SPAN® 85 system. This result revealed that the PBS/squalene/SPAN® 85 emulsion contained only the lipophilic emulsifier SPAN® 85 and rendered an emulsion with a high affinity to the oily phase, whereas the emulsion PEG-b-PLACL/squalene or PEG-b-PLACL/squalene/SPAN® 85 had a hydrophilic polymeric emulsifier and rendered an emulsion with a high affinity to the aqueous phase.

TABLE 4

| Component | | | | |
|---|---|---|---|---|
| Aqueous phase | Oily phase | HLB | Emulsion type | Particle size |
| PEG-b-PLACL/PBS | Squalene | 15.0 | O/W emulsion | ~1-10 μm |
| PEG-b-PLACL/PBS | Squalene/SPAN® 85 | 7.5[a] | W/O/W emulsion | <1 μm |
| —/PBS | Squalene/SPAN® 85 | 1.8 | W/O emulsion | — |

[a]$HLB_{mix} = X_{PEG-b-PLACL} \times HLB_{PEG-b-PLACL} + X_{SPAN85} \times HLB_{SPAN85}$, where X is the weight fraction of each surfactant.

Figure 10:
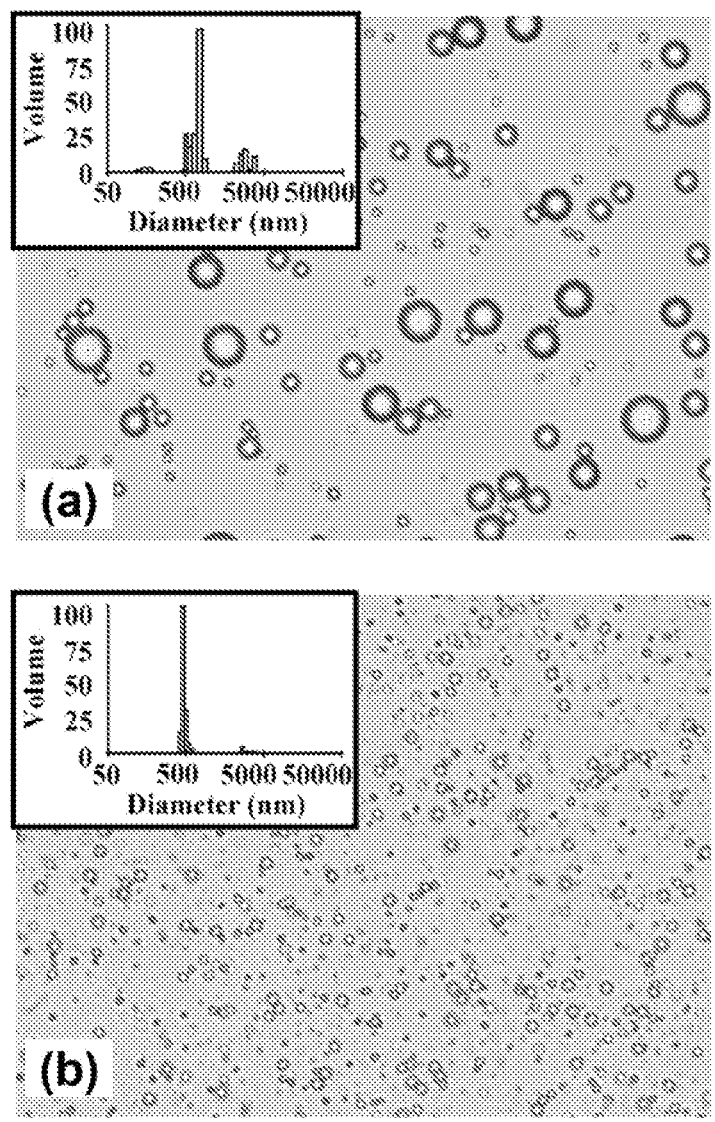
FIGS. 10(a)-10(b) show microscopic aspects and laser light scattering analysis of polymer-emulsified formulations (a) PEG-b-PLACL/squalene and (b) of PEG-b-PLACL/squalene/SPAN® 85.

The emulsion drops were invisible under an optical microscope since they were crowded in the dispersed phase. The size distribution of the emulsion was investigated by redispersing the emulsion in the continuous phase and measuring the size with a microscope and particle sizer. As shown in FIG. 10a, the emulsion PEG-b-PLACL/squalene was composed of nonhomogeneous particles with a bimodal distribution. Two different sizes of particles were observed, relatively large particles of about 10 μm and smaller particles of about 1 μm. By contrast, homogeneous fine particles less than 1 μm were observed with an optical microscope when redispersing the PEG-b-PLACL/squalene/SPAN® 85 in the PBS (FIG. 10b), The dynamic light scattering pattern showed a unimodal distribution with an average diameter of 457.7±25.8 nm. Stabilized particles of ~1-10 μm in diameter are appropriate for uptake by antigen-presenting cells (APCs) to facilitate the induction of potent immune responses due to the pseudo-natural targeting of antigens.

In vitro Protein Release from Various Formulations

Figure 11:
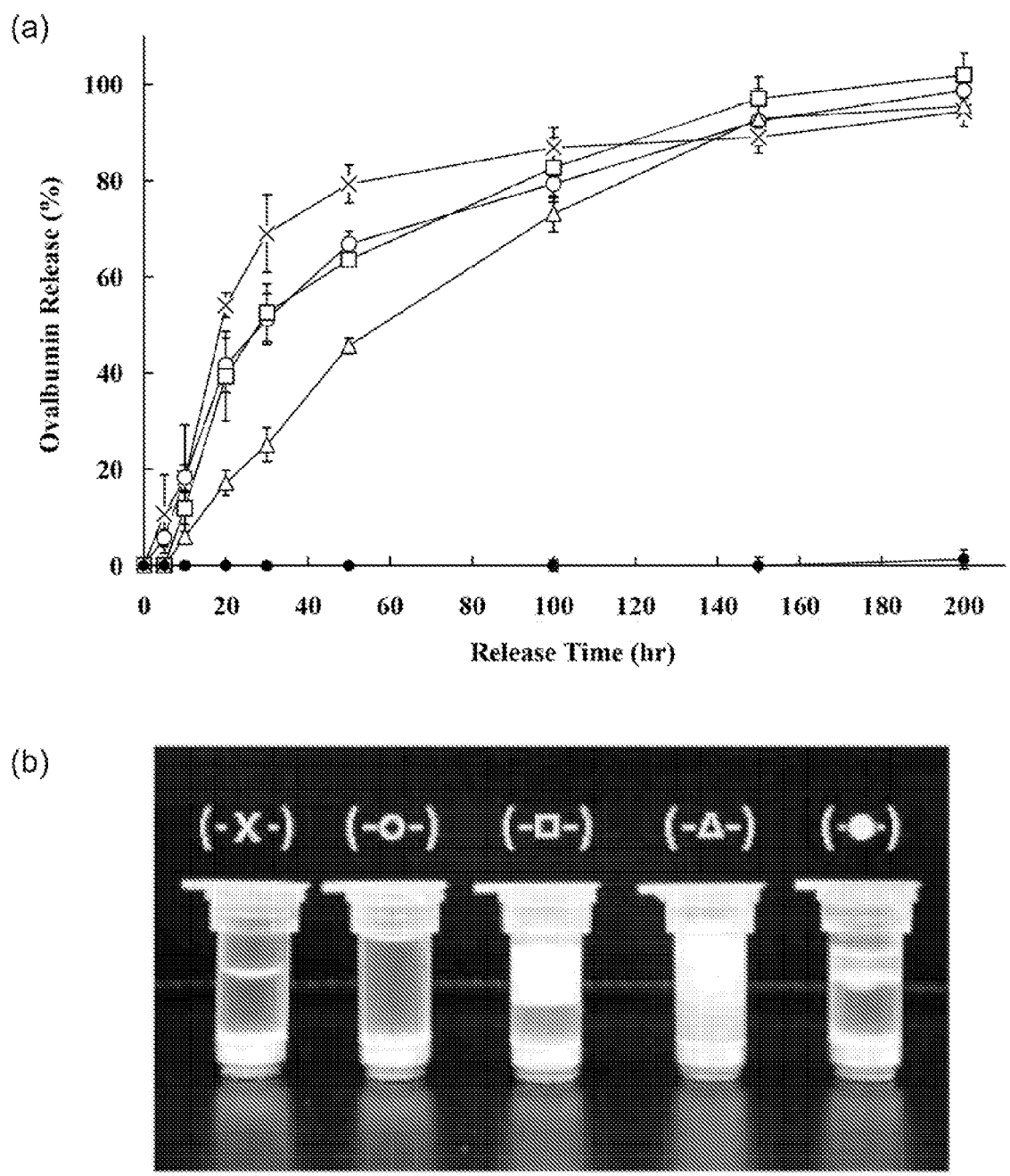
FIG. 11(a) is a graph showing the cumulative release of OVA from various formulations. (-x-) No adjuvant, (open circle) the aqueous solution PEG-b-PLACL, (open square)

FIG. 11 shows the cumulative release of OVA from various formulations: (-x-) no adjuvant, (open circle) the aqueous solution PEG-b-PLACL, (open square) the O/W emulsion PEG-b-PLACL/Squalene, (open triangle) the W/O/W emulsion PEG-b-PLACL/squalene/SPAN® 85, (filled circle) the W/O emulsion PBS/squalene/SPAN® 85. Initially, a fast release was observed in the case of OVA without adjuvant from which more than 80% of loaded OVA were released into the outside PBS medium within the first 50 h. The polymer aqueous solution or PEG-b-PLACL/squalene emulsion allowed a slight delay but the protein was quickly released. The emulsion PEG-b-PLACL/squalene/SPAN® 85 released less than 50% of OVA during the same period of time. Afterwards, the protein release increased continuously until it reached an equilibrium concentration in the inside and outside of the dialysis device. The PBS/squalene/SPAN® 85 emulsion presented a well depot effect on OVA so that hydrophilic OVA was slowly released over 200 h.

FIG. 11b shows the recovered formulations after 200 h experiments. Phase separation occurred in the formulation PBS/squalene/SPAN® 85. By contrast, the PEG-b-PLACL-based emulsion remained stable with clear layers of water at the bottom. The protein (ovalbumin as an example) initially encapsulated within the emulsion was almost released at this time, which indicated that the hydrophilic bioactive agents (or antigens) trapped within the polymer-emulsified oily emulsion were released from the core oil to the surface mostly by diffusion, but also to a lesser extent by degradation mechanisms and emulsion breaks, Immunogenicity Studies in Mice Physicochemical characterization showed that various emulsions provide different size ranges of particles and different antigen controlled-release mechanisms so that the emulsified particles could serve as either carriers or vehicles to deliver antigens to APCs in a targeted and prolonged manner. To evaluate the potential application of these polymer-based emulsions as adjuvant, BALB/c mice were vaccinated subcutaneously with OVA using various formulations. Table 5 shows the B-cell response to OVA-formulations with different adjuvants. Following immunization, the antigen-specific antibody IgG response in the group of OVA alone was undetectable in an initial serum dilution of 1:50 at week 2, and less than $10^4$ serum titers were detected at week 4. However, the serum antibody IgG titers as well as isotypes IgG1 and IgG2a were significantly enhanced for the group of PEG-PLACL/squalene or PEG-b-PLACL/squalene/SPAN® 85- or alum-formulated OVA in comparison to the free OVA group ($p<0.05$). For IgG responses, the ratio between the geometric mean titer (G MT) obtained with PEG-b-PLACL/squalene/SPAN® 85-formulated OVA vaccine and the GMT obtained with vaccine alone was found to be 19.9 at week 4, in comparison with the group of PEG-b-PLACL/squalene being 2.4 and the group of alum being 6.3. PEG-b-PLACL/squalene-formulated OVA induced comparable levels of serum antibody titers as alum-formulated OVA within 10 weeks. The highest antibody responses were elicited in the group of PEG-b-PLACL/squalene/SPAN® 85-formulated OVA, in which statistical significance with respect to alum was detected at weeks 2 and 4, that is, in the early stages after immunization. The immunogenicity increase was probably due to appreciable particle size and/or carrier/depot activity.

homogeneous distribution are more stable, which are however strongly influenced by the optimization of the surfactant system and the emulsification process. Homogenization of PEG-b-PLACL-containing aqueous solution and the SPAN® 85-contained oily phase provides a potential way of stabilizing emulsified particles both at storage and at postinjection stage conditions.

TABLE 5

[OK]

| Formulation | IgG | | |
| --- | --- | --- | --- |
| | Week 2 | Week 4 | Week 6 |
| No adjuvant | <50 | 5,400 (2,200-13,300) | 79,200 (62,000-101,100) |
| PEG-b-PLACL/Squalene | 400$^a$ (50-2,800) | 12,700 (4,000-40,400) | 101,800 (69,200-149,700) |
| PEG-b-PLACL/squalene/SPAN ® 85 | 3800$^{a,b}$ (3,200-4,500) | 107,500*# (63,300-182,500) | 163,700$^a$ (85,600-312,900) |
| Alum | 500$^a$ (100-2,600) | 34,000$^a$ (20,300-57,000) | 124,000$^a$ (79,800-192,700) |

| Formulation | IgG | | IgG 1 | IgG 2a |
| --- | --- | --- | --- | --- |
| | Week 8 | Week 10 | Week 4 | Week 4 |
| No adjuvant | 90,400 (55,100-148,300) | 74,700 (50,300-111,000) | 18,100 (9,500-34,600) | 100 (80-200) |
| PEG-b-PLACL/Squalene | 124,800 (69,100-225,500) | 67,100 (28,500-157,700) | 49,600 (15,200-161,600) | 500 (100-2,750) |
| PEG-b-PLACL/squalene/SPAN ® 85 | 182,000$^a$ (129,600-255,600) | 130,100$^a$ (99,100-170,700) | 274,600$^{a,b}$ (183,200-411,700) | 5,500$^a$ (2,000-14,900) |
| Alum | 138,600 (74,900-256,500) | 99,100 (70,000-140,300) | 112,400$^a$ (83,200-152,000) | 2,600$^a$ (1,120-6,200) |

BALB/c mice were vaccinated three times subcutaneously (week 0, 2, 4) with dose of 0.5 µg OVA. Sera were collected from blood and the antibody titers were measured by ELISA. The data are presented as geometric mean titers with 95% confidence intervals of five mice per group.
$^a$P < 0.05: Comparison with free OVA group at the same time point.
$^b$P < 0.05: Comparison with alum-formulated OVA group at the same time point. <50 means undetectable in an initial dilution of 1:50.

T-cell proliferation and cytokine responses were measured in the splenocytes following restimulation of the cells in vitro with OVA antigen. FIG. 12a showed that following one immunization, OVA alone did not induce antigen-specific proliferative response well due to the low dosage of antigen so that the stimulation index of the OVA/PBS group was only slight higher than the threshold value. Once OVA was formulated with the polymer-based emulsion or adsorbed to alum, positive T-cell proliferative response was induced. FIG. 12b shows that sufficiently elevated IFN-γ secretion, a predominant T helper type 1 cytokine, was detected in the supernatants of splenocyte collected from mice treated with PEG-b-PLACL/squalene- and PEG-b-PLACL/squalene/SPAN® 85-formulated OVA, following in vitro restimulation of splenocytes with OVA. By contrast, T helper type 2 cytokine IL-4 was measured at the same or reduced level as OVA alone.

Discussion

Delivery of antigens in a targeted or prolonged manner can be performed with different emulsion-type adjuvants and can be achieved in specific surfactant systems. Surfactants as emulsifiers can be defined by their hydrophilic-lipophilic balance (HLB) value, which gives information on their relative affinity to both aqueous and oily phases. In this study, the droplet test and in vitro release data showed that the squalene/SPAN® 85 oil solution contained an emulsifier of low HLB value ($HLB_{SPAN®85}$=0.8), which rendered a O/W emulsion. By contrast, the PEG-b-PLACL/squalene system with a high HLB value emulsifier rendered an O/W emulsion. Finally, the emulsion PEG-b-PLACL/squalene/SPAN® 85 is composed of two emulsifiers and renders a water-in-oil-in-water (W/O/W) multiphase emulsion (FIG. 13). From a viewpoint of emulsion stability, oil droplets with a small particle size and A polymer can play different roles in a particulate delivery system. The most direct role is to provide a matrix or a vehicle that builds the microparticle. Degradable PLG, PLA, and PCL used for vaccine or protein delivery have mostly been in the form of injectable microspheres or implant systems. Such systems require complicated fabrication processes using organic solvents and may cause denaturation when antigens (virus or proteins) are to be encapsulated. Moreover, the systems require polymers with high molecular weight (generally >100,000 Da), which require severe polymerization conditions (extreme temperature and pressure and toxic catalysts). By contrast, amphiphilic copolymers such as poly (ethylene glycol)-block-poly(propylene sulphide)-blockpoly (ethylene glycol) and poly(ethylene glycol)-block-polyoxypropylene-block-poly(ethylene glycol) (known as PLURONIC® or Poloxamers) could be formed as polymersomes, as oil free thermosensitive hydrogels or as a surfactant to render an emulsion (known as TiterMax®) in vaccine delivery systems. These polymeric emulsifiers render stable emulsions and elicit both potent humoral and cellular immune responses with respect to other formulations, using OVA as model. Their use in human vaccine delivery is however problematic because they are rather toxic and nonbiodegradable. We have attempted to study the effects of polymer aqueous solution or polymer-based emulsions on the activation and antigen-presenting functions of bone marrow-derived dendritic cells to understand the biological interactions and immunological mechanisms of action. Our findings indicated that PEG-b-PLACL-based formulations were biologically inert in dendritic cells (data not shown). These formulations probably could not act as immunostimulatory adjuvants for dendritic cells of the innate system but could be used as vaccine delivery systems instead.

To our knowledge, we are the first group to investigate the synthetic, amphiphilic, bioresorbable polymer as an emulsification agent to stabilize aqueous/oily interfaces. The emulsified vaccine delivery systems have several advantages over traditional vaccine adjuvants. Firstly, synthetic polymeric emulsifier is reproducible from batch to batch, and the relative hydrophobic/hydrophilic balance can be easily manipulated by the amounts of monomer used, thus producing a broad range of emulsifier characteristics, Secondly, unlike antigen adsorption onto alum, the system allows either the surface attachment or encapsulation of antigens, and the emulsified formulation can be stored at or below room temperature as a stock before injection. Moreover, the acidic condition is not required in the preparation of PEG-b-PLACL and/or SPAN® 85 emulsified delivery systems because both are nonionic emulsifiers. Thirdly, bioresorbable polymeric emulsifiers, with a hydrophobic block that is degradable, show bulk degradation and further resorb in vivo. Fourthly, the raw materials for polymer synthesis described here are commercially available and frequently used for temporary therapeutic applications. Furthermore, the formulation is easy for preparation, that is, no complicating processes or supplemental equipment are required and thus the cost is reduced. Moreover, the polymer-emulsified delivery system is free of organic solvents, in contrast to the common polymeric microspheres. Fifthly, with only 5% of oil included in the vaccines (see MATERIALS AND METHODS: Mice and Immunizations), the W/O/W emulsion increases injectability and conceptually diminishes local reactions, which is encountered by the W/O type vaccines produced from the same oil. Finally, from the immunity viewpoint, antigen-specific antibody titers and T-cell proliferative responses as well as IFN-γ responses were significantly enhanced (p<0.05) to ovalbumin after being formulated with the PEG-b-PLACL-based emulsions. These features are of great interest for local delivery of bioactive agents, especially for application in candidate vaccine delivery systems.

Conclusion

With the aim of enhancing vaccine potency, we used a bioresorbable diblock tri-component copolymer PEG-b-PLACL as an emulsifier and rendered an O/W or W/O/W multiphase emulsion when the polymer aqueous solution was homogenized with squalene or the squalene/SPAN® 85 mixture. Novel polymer-emulsified formulations have high affinity to water so that the stock OVA-containing emulsion could be redispersed into PBS before injection, thus resulting in fluid emulsion (only 5% of oil within the emulsion) with homogeneous particles ranging between 1 and 10 μm. The emulsified particles could serve as either carriers or vehicles to deliver biologically active agents (ovalbumin as an example) to APCs in a targeted and prolonged manner, thus effectively enhancing immunity. These formulation have potential to be used in adjuvants for prophylactic and therapeutic vaccine candidates. Such applications include single-dose multivalent vaccine development and via alternative immunization routes, such as intramuscular or transdermal administration.

Example 4

Previously, based on the bioresorbable diblock tri-component co-polymer poly(ethylene glycol)-block-poly(lactide-co-ε-caprolactone) (PEG-b-PLACL), we developed a water-in-oil-in-water multiphase emulsion-type vaccine delivery system called PELC. In this emulsion, PEG-b-PLACL served as a hydrophilic emulsifier and SPAN® 85 acted as a hydrophobic emulsifier to stabilize the water/squalene interface, resulting in a stable and homogeneous nanoemulsion. Preliminary immunogenicity studies in mice using ovalbumin as a model antigen showed that antigen-specific antibody titers, T-cell proliferative response, and interferon-γ (IFN-γ) secretion increased significantly after formulation with PELC. Thus, this approach is of great interest for applications in prophylactic and therapeutic vaccination. In preparation for a potential shortage of pandemic influenza vaccine, we aimed to increase the efficacy of vaccine candidates via formulation with PELC. In the work described here, a single-dose immunization was performed using inactivated H5N1 virus adjuvanted with PELC. The PELC-formulated hemagglutinin (HA; 0.5 μg) of inactivated virus induced more potent antigen-specific antibodies, hemagglutination inhibition, and virus neutralization than HA (5 μg) of non-adjuvanted virus, demonstrating the antigen economization of the PELC-based vaccine. Moreover T-cell proliferative responses as well as IFN-γ and interleukin-4 (IL-4) secretion were significantly enhanced after formulation with the PELC emulsion. These results demonstrate that PELC could play an important role in the influenza pandemic vaccine development (Huang et al. (2009) "Enhancement of potent antibody and T-cell responses by a single-dose, novel nanoemulsion-formulated pandemic influenza vaccine" *Microbes and infection* 11: 654-660, which is herein incorporated by reference in its entirety).

Materials and Methods

Vaccine Preparation

The vaccine used in this study was the formalin-inactivated whole-virus vaccine NIBRG-14, which was kindly supplied by the UK National Institute of Biological Standard and Control, NIBSC. The vaccine was derived from a reassorted H5N1 vaccine strain containing modified HA and neuraminidase (NA) from a highly pathogenic avian influenza strain A/Vietnam/1194/2004 and propagated in Madine-Darby canine kidney (MDCK) cells. Formalin-inactivated vaccines were prepared with 0.1% formalin at 37° C. for 24 h. The HA content was determined by single radial diffusion (SRD). Production details for the H5N1 vaccine candidate are reported elsewhere.

Adjuvant Preparation

The diblock co-polymer PEG-b-PLACL was synthesized by the ring-opening polymerization of lactide and ε-caprolactone on monomethoxy PEG as previously described. The PEG-b-PLACL consisted of 75 wt % hydrophilic block PEG and 25 wt % lipophilic block PLACL. The calculated hydrophilic lipophilic balance (HLB) value was 15 with a molecular weight of 7000. PELC is an emulsion-type vaccine delivery system based on PEG-b-PLACL, SPAN® 85, and squalene. Briefly, a PEG-b-PLACL-containing aqueous solution (120 mg dissolved in 0.8 mL of phosphate-buffered saline (PBS)) and 1.1 mL of an oily phase containing a squalene/SPAN® 85 mixture (85/15 v/v) were emulsified using a POLYTRON® PT 3100 homogenizer (Kinematica AG, Swiss) at 6000 rpm for 5 min. The emulsified formulation was stored at 4° C. until use. The PELC-adjuvanted vaccine was formulated by re-dispersing 200 μL of the stock PELC emulsion in 1800 μL of bulk vaccine before injection. The size distribution of the emulsion droplets was determined with a microscope (Olympus DP70) and the laser light scattering technique (Brookhaven 90 plus particle size analyzer, Brookhaven Instruments Limited).

Mice and Immunizations

Five-week-old female BALB/c mice were obtained from the National Laboratory Animal Breeding and Research Center (Taipei, Taiwan) and acclimatized for at least one week at the animal facility of the National Health Research Institutes (NHRI, Miaoli, Taiwan) prior to use. To investigate the potency of a single-dose of H5N1 influenza vaccine, all mice were vaccinated intramuscularly (i.m.) with one of two different doses (0.5 µg or 5 µg HA) administered with or without PELC. Serum and tissue collection were performed to determine B- and T-cell responses. Serum samples were collected from immunized mice and antibody titers were determined by enzyme-linked immunosorbent assay (ELISA) as well as by hemagglutination inhibition titration, and viral neutralizing assays.

ELISA Immunoassay

The presence of NIBRG-14-specific antibodies in the sera was determined via ELISA. Briefly, 96-well microtiter plates were coated with 100 mL of dilute inactivated virus (1 µg/mL) and incubated overnight at room temperature. The coated plates were washed once with PBS containing 0.05% TWEEN® 20 (Sigma) and blocked with 1% bovine serum albumin (BSA, SIGMA™) in PBS at room temperature for 2 h. Diluted sera (starting dilution 1:1000, serial two-fold serum dilutions) from immunized mice were applied to the blocked wells at room temperature for 2 h. After another wash, HRP-conjugated goat anti-mouse IgG (ICN Cappel, 1:5000) was added to all wells at room temperature for 30 min. The assay was developed using the substrate solution 2, 20-azino-di(3-ethyl-benzothiazoline-6-sulfonate) (ABTS® Peroxidase. KPL) for 20 min at room temperature and shielded from light. Plates were read at 405 nm with an ELISA plate reader (THERMO MULTISKAN® spectrophotometer, Vantaa, Finland). For isotype determination, 100 µL of HRP-conjugated rabbit anti-mouse IgG1 (AbD Serotec, Kidlington, UK, 1:5000) or HRP-conjugated rabbit anti-mouse IgG2a (AbD Serotec, Kidlington, UK, 1:2000) was added instead of anti-mouse IgG. The titers were expressed based on the inverse of the final dilution that gave two-fold greater absorbance than the pre-immune sera.

Hemagglutination Inhibition (HI) Titration

The HI test was based on the ability of the specific anti-influenza antibodies to inhibit hemagglutination of turkey red blood cells (RBCs) by influenza virus HA. Non-specific inhibitors of agglutination were removed by heat treatment and addition of receptor-destroying enzymes. After pretreatment, serum samples (two-fold dilutions starting at an initial dilution of 1:10) were incubated with four hemagglutination units of influenza strain. Turkey RBCs were then added and agglutination inhibition was scored. The serum titer was expressed as the reciprocal of the highest dilution that demonstrated complete HI. The seroprotection rate (SPR, %) was calculated from the proportion of mice achieving a post-vaccination titer ≧40.

Virus Neutralization (VN) Assay

The NIBRG-14 virus in 200 TCID50 (50% tissue culture infective dose) per well was incubated with two-fold-diluted mice sera at a starting dilution of 1:40. The mixtures of virus and serum were transferred to monolayers of MDCK cells and incubated at 37° C. and 5% $CO_2$ for 4 days. The neutralizing titer was expressed as the reciprocal of the highest serum dilution at which the infectivity of the H5N1 virus 200 TCID500 for MDCK cells was completely neutralized in 50% of the wells. Infectivity was identified by the presence of cytopathy on Day 4 and the titer was calculated using the ReedeMuench method.

Statistical Analysis

The statistical significance (P<0.05) was determined by performing a two-tailed Student's t-test on log-transformed values.

T-Cell Immune Assay

It has been demonstrated that 7-14 days post-immunization is a reasonable time point for detecting influenza-specific T-cell proliferation, We chose the twelfth day after immunization as an endpoint. The mouse spleen was removed aseptically twelve days after immunization and transferred to a tube containing 1 mL of RPMI-1640 culture medium (cRPMI) (SAFC, Kansas, USA) with 2 Mm L-glutamine and supplemented with 25 mM HEPES (Gibco, Invitrogen, NY, USA), 0.05 mM 2-mercaptoethanol, 10% heat-inactivated fetal bovine serum (FBS; HyClone/Perbio), 100 µg/ml streptomycin, and 100 U/ml penicillin. Cell suspensions were prepared by mashing the spleen through a cell strainer with a syringe plunger. The resulted suspension was collected in a 50-mL tube and centrifuged at 1000 rpm for 5 min. To remove erythrocytes, the cell pellet was resuspended in 5 mL of RBC lysis buffer (150 mM $NH_4Cl$, 1 mM $KHCO_3$ and 0.1 mM EDTA (pH 7.3), Biolegend, CA) and incubated at room temperature for 1 main. The reaction was then terminated with 20 mL of RPMI-1.640 and the mixture was centrifuged for 5 min. The pellet was washed twice with cRPMI and resuspended in 5 mL of cRPMI. After cell counting with a hemacytometer by the trypan blue dye exclusion, U-bottomed 96-well plates were seeded with $2 \times 10^5$ cells in cRPMI at a total volume of 200 µL per well. Cells were stimulated in triplicate in the presence or absence of 2.5 µg HA/mL of inactivated NIBRG-14 virus. Concanavalin A (Con A, 5 µg/mL, Sigma) was used to induce a maximal proliferative response. Plates were then incubated for 4 clays at 37° C. and 5% CO2 in air. Cellular proliferation was assessed with the addition of 1 µCi of tritiated methylthymidine (Perkin Elmer, Mass.) to the cell suspension for the final 16 h of culture. IFN-γ and IL-4 concentrations in the supernatants were measured by ELISA with paired antibodies according to the manufacturer's instructions (R&D Systems, Abingdom).

Results

Formulation of Inactivated Influenza Virus with PELC

The PELC-formulated influenza candidate vaccine consisted of an inactivated virion and a pre-emulsified PELC stock (see Materials and methods: Adjuvant preparation). Prior to the injection, the PELC stock and inactivated virions were mixed to form homogeneous particles. The size distribution of the particles ranged from 200 to 400 nm in diameter (FIG. 14), which was consistent with the definition of nanoemulsion. Importantly, it has been reported that this nanoscale dimension is conducive to uptake by antigen-presenting cells, which facilitates the induction of potent immune responses.

Determination of NIBRG-14-Specific Antibodies Elicited in BALB/C Mice

To evaluate whether protective antibodies were induced by a single immunization with the candidate vaccine, BALB/c mice were intramuscularly immunized with 0.5 µg or 5 µg HA of inactivated NIBRG-14 virus formulated with or without PELC. Table 6 shows NIBRG-14-specific IgG, IgG1, and IgG2a antibodies elicited in BALB/c mice following a single intramuscular dose of H5N1 inactivated virus vaccine. The elicited antigen-specific antibodies are shown in Table 6. The results demonstrated that the specific anti-virus IgG, IgG1, and IgG2a titers induced by the PELC-formulated inactivated virus were significantly higher than those induced by non-adjuvanted inactivated virus in both the 0.5 µg and 5 µg HA groups (P 0.05). Another advantage of vaccination with PELC-formulated inactivated virus was revealed at the fourth week after administration: the IgG titers induced by PELC formulated with 0.5µ HA of inactivated virus were one order higher than those induced by 5 µg HA of inactivated virus. The titers induced by 5 µg HA were still lower than those induced by one-tenth of the same amount of PELC-formulated antigen (0.5 µg HA) at the same time point.

TABLE 6

| Vaccine | GMT ± SE | | | |
|---|---|---|---|---|
| | No adjuvant | | Formulated with PELC | |
| IgG | 0.5 µg | 5 µg | 0.5 µg | 5 µg |
| Week 2 | <1000 | 2000 ± 500* | 1800 ± 900* | 5900 ± 1700*,# |
| Week 4 | 1400 ± 200 | 4000 ± 1100* | 11,300 ± 4700* | 29,000 ± 8000*,# |
| Week 8 | 7100 ± 700 | 16,000 ± 4500* | 45,250 ± 12,600*,# | 64,000 ± 15,000*,# |
| Week 12 | 6050 ± 1000 | 10,800 ± 2000 | 39,000 ± 7600*,# | 55,700 ± 6400*,# |
| Week 18 | 5650 ± 2000 | 13,100 ± 4300 | 21,500 ± 10,800* | 42,200 ± 7800*,# |
| Week 26 | 7100 ± 2400 | 14,500 ± 4800 | 23,800 ± 9000* | 48,500 ± 7800*,# |
| IgG1 at week 8 | 3300 ± 800 | 7300 ± 3400 | 17,450 ± 6800* | 29,000 ± 16,000*,# |
| IgG2a at week 8[a] | 7100 ± 2400 | 22,600 ± 4300 | 107,600 ± 45,250*,# | 105,000 ± 25,900*,# |

The data are presented as geometric mean titers (GMTs) with standard errors (SE) of eight mice per group.
*$P < 0.05$: comparison with the group of 0.5 µg HA without adjuvant at the same time point.
$P < 0.05$: comparison with the group of 5 µg HA without adjuvant at the same time point. <1000 means undetectable in an initial dilution of 1:1000.
[a]Titrations do not reflect absolute concentrations as can be seen in the IgG2a subtype assays that are more sensitive than the total IgG assays.

Hemagglutination Inhibition (HI) Activities of Elicited Antisera

The HI activity assay is the most common way to determine the efficacy of an influenza vaccine. We determined HI activity using turkey erythrocytes incubated with sera obtained from the vaccinated groups. Table 7 shows that HI antibody responses were elicited in BALB/c mice following a single intramuscular dose of inactivated H5N1 virus vaccine formulated with or without PELC. Following a single injection, sera from the mice vaccinated with 0.5 µg HA of non-adjuvanted inactivated virus elicited an HI geometric mean titer (GMT) of 6 and 9 at Weeks 2 and 4, respectively. The highest GMT responses were 59 at Week 12 and 33 at Week 26. When the amount of non-adjuvanted virus administrated was increased to 5 µg HA, the HI titer was slightly enhanced at Weeks 2, 4, and 8. There were however no statistically significant differences (Pzl) in HI titers between the 0.5 μg and 5 μg HA groups. By contrast, the PELC-adjuvanted vaccines were capable of inducing higher HI titers than those developed from the virus alone (P<0.05). Even in the group of PELC-adjuvanted, 0.5 μg HA of inactivated virus, the HI titer was significantly higher than that induced by non-adjuvanted, 5 μg HA of inactivated virus. Moreover, the seroprotection of those groups immunized with inactivated virus alone never reached 100%. In contrast, after formulation with PELC, seroprotection easily reached 100% in both 0.5 μg HA and 5 μg HA groups, which indicated the merit of PELC-adjuvanted inactivated influenza virus.

TABLE 7

| Vaccine | GMT ± SE (SPR, %) | | | |
|---|---|---|---|---|
| | No adjuvant | | Formulated with PELC | |
| | 0.5 μg | 5 μg | 0.5 μg | 5 μg |
| Week 2 | <10 (0%) | 20 ± 13* (38%) | 44 ± 9* (75%) | 80 ± 24*,# (100%) |
| Week 4 | <10 (14%) | 22 ± 11 (50%) | 62 ± 20*,# (100%) | 108 ± 21*,# (100%) |
| Week 8 | 24 ± 10 (57%) | 26 ± 12 (63%) | 95 ± 34*,# (100%) | 238 ± 44*,# (100%) |
| Week 12 | 59 ± 23 (86%) | 44 ± 25 (63%) | 108 ± 38 (100%) | 422 ± 107*,# (100%) |
| Week 18 | 49 ± 39 (86%) | 52 ± 26 (63%) | 131 ± 36 (100%) | 243 ± 58*,# (100%) |
| Week 26 | 33 ± 13 (57%) | 37 ± 25 (63%) | 88 ± 37 (86%) | 184 ± 45*,# (100%) |

The data are presented as geometric mean titers (GMTs) with standard errors (SE) of eight mice per group. The seroprotection rate (SPR, %) is the percentage of mice achieving a post-vaccination titer ≧40.
*P < 0.05: comparison with the group of 0.5 μg HA without adjuvant at the same time point.
P < 0.05: comparison with the group of 5 μg HA without adjuvant at the same time point. <10 means undetectable in an initial dilution of 1:10.

Virus Neutralization (VN) Activities of Elicited Antisera VN assays were performed to provide a more functional measure of vaccine-induced immunity. As shown in Table 8, the neutralizing antibody titers were slightly enhanced when the amount of non-adjuvanted antigen administered was increased. In contrast, when the vaccine was formulated with PELC, the neutralizing antibody titers were dramatically enhanced. The highest neutralizing antibody titers were induced by the PELC-adjuvanted 5 µg HA group. The VN capability of PELC-formulated, inactivated virus was complementary to its adjuvanticity demonstrated by HI titers. Thus, a combination of PELC and inactivated virus may induce sufficient and sustainable protective antibodies. Importantly, 0.5 µg HA of PELC-formulated, inactivated virus could induce higher antibody titers, higher HI activity, and higher VN activity than 5 µg HA of inactivated virus alone. These results indicated that inactivated virus formulated with PELC could not only facilitate a decrease in antigen dose, but also an increase in the humoral protection.

T-Cell Proliferation and Cytokine Responses to PELC-Formulated Antigens

We next sought to determine whether T-cell responses could also be enhanced when antigen was formulated with PELC. Twelve days after intramuscular immunization with 0.5 µg HA of inactivated virus in PBS or PELC, single-cell suspensions were prepared from the mouse spleen and restimulated in vitro in the presence of inactivated virus for 4 days. FIG. 15A shows that following one vaccination, the virus alone did not induce a notable antigen-specific proliferative response. The elicited Stimulation Index (SI), which is the ratio of the mean counts per minute (cpm) with antigen to the cpm without antigen, was only slightly higher than the control value. However, once the PELC-formulated vaccine candidate was administered, a positive T-cell proliferative response was induced and the SI value was about two-fold higher than that of the non-adjuvanted group. In addition, the IFN-γ and IL-4 concentrations detected in the splenocyte supernatants of the PELC group were significantly higher than those of the nonadjuvanted group (FIG. 15B). IFN-γ is a predominant T helper type 1 (Th1) cytokine relevant to virus-specific cytotoxic T lymphocyte (CTL) activity, while IL-4 is a common T helper type 2 (Th2) cytokine. Therefore, an antigen formulated with PELC may not only increase the humoral protection but also enhance both Th1 and Th2 responses. These results indicated that PELC may have applications in single-dose immunization and could play an important role in influenza pandemic preparedness.

TABLE 8

| | GMT ± SE | | | |
|---|---|---|---|---|
| | No adjuvant | | Formulated with PELC | |
| | Vaccine 0.5 µg | 5 µg | 0.5 µg | 5 µg |
| Week 2 | <40 | <40 | <40 | <40 |
| Week 4 | <40 | <40 | 53 ± 21 | 211 ± 74*,# |
| Week 8 | 49 ± 26 | 56 ± 32 | 180 ± 59*,# | 381 ± 54*,# |
| Week 12 | 207 ± 56 | 144 ± 61 | 261 ± 134 | 1452 ± 154*,# |
| Week 18 | 176 ± 55 | 125 ± 67 | 293 ± 195 | 695 ± 90*,# |
| Week 26 | 64 ± 23 | 66 ± 34 | 92 ± 56 | 333 ± 39*,# |

The data are presented as geometric mean titers (GMTs) with standard errors (SE) of eight mice per group.
*$P < 0.05$: comparison with the group of 0.5 µg HA without adjuvant at the same time point.
$P < 0.05$: comparison with the group of 5 µg HA without adjuvant at the same time point.
<40 means undetectable in an initial dilution of 1:40.

Discussion

Alum-formulated H5N1 influenza vaccines have demonstrated that a prime/boost vaccination schedule is required to generate effective protection against either heterologous or homologous viral strains. After priming, the virus-neutralizing antibody levels were below the detection limit for groups that received doses ranging from 0.001 to 3.75 µg HA antigens with or without alum. However, the antibody titers increased substantially and virus-neutralizing antibodies were detectable after boosting with the same amount of antigen. It was reported that after the prime/boost immunization with inactivated H5N1, the induced levels of protective antibodies were not statistically different between the groups immunized with 0.2 µg or 2 µg HA antigens. In addition, there were no differences between the groups immunized with or without alum. It was also reported that the prime/boost vaccination with inactivated H₂N2 consisting of 1.5 µg HA mixed with alum induced a systemic response equivalent to that of a non-adjuvanted 15 mg HA vaccine. Here, we demonstrated that a single-dose administration of PELC-formulated virus significantly induced virus-neutralizing antibodies and had a dose-dependent effect on HI and VN responses. In contrast, no dose-dependent responses were evident in the non-adjuvanted groups. In terms of the longevity of the induced antibody responses, there was no significant difference between the response to the virus alone and to the versus formulated with PELC. In both cases, the total IgG titers peaked at Week 8 and fluctuated, decreased slightly until Week 26. Meanwhile, the HI and VN antibody levels reached a high peak at Week 12 and then declined until Week 26. These results have established a potential application of PELC-formulated vaccines in pandemic influenza preparedness. PELC-adjuvanted immunization may be particularly helpful in preventing a vaccine shortage since its efficacy permitted a decrease in antigen dosage and its single-dose formulation eliminated the need for boosting.

Since O/W emulsions can quickly induce a strongly immunocompetent environment at the site of injection, they are more efficient than alum for human vaccination. Furthermore, recent clinical data have demonstrated that pandemic H5N1 vaccines formulated with O/W emulsions induce seroconversion and cross-neutralization superior to that of non-adjuvanted and alum-formulated vaccines. Despite the benefits of O/W emulsions, one drawback to the use of TWEEN® 80 as a hydrophilic emulsifier is that it attacks cell walls and thus is potentially toxic. One viable alternative is the hydrophilic emulsifier PEG-b-PLACL, which has several advantages over TWEEN® 80. Firstly, PEG-b-PLACL is derived from the Food and Drug Administration (FDA)-approved PEG, polylactides, and poly(3-caprolactone) and is thus expected to pass all safety tests. Secondly, polymeric emulsifiers generally result in more stable emulsions and more potent humoral and cellular immune responses than small molecule-emulsified formulations. Finally, degradable emulsifiers allow stabilization of emulsion particles during storage and allow disintegration of the system after the injection. These characteristics of PEG-b-PLACL-emulsified vaccines demonstrate the potential safety and efficacy of PELC-formulated vaccines.

For over a decade, the advisory committees in the North America have cautioned that influenza vaccine-induced antibodies decline more rapidly in the elderly. It is believed that the aging population is most susceptible to influenza infection. Recently, an effective vaccination was correlated with the induction of Th1 cytokine IFN-γ, especially in the elderly, who undergo a shift toward Th2 cytokine (such as IL-4) production and a relative reduction in CTL activity as they age. Therefore, increasing IFN-γ induction via vaccination is thought to be an important strategy for overcoming the age-related influenza susceptibility. Toward this end, PELC may be a potent adjuvant due to its stimulation of antigen-specific T-cell proliferation and IFN-γ secretion. PELC-formulated virus also upregulated IFN-γ and IL-4 in splenocytes and increased IgG1 and IgG2a antibody levels more than virus alone. The vaccine formulation with PELC however did not significantly skew the immune response toward Th1 or Th2 (Table 6 and FIG. 15B). These results implied that the antigens adjuvanted with PELC might dramatically enhance the immunogenicity of vaccine candidates. Further investigations are under way to examine the combinations of the PELC vaccine delivery system and immunostimulatory adjuvants, such as CpG oligodeoxynucleotide, in order to manipulate the immune response and alter the Th1/Th2 balance. In conclusion, we found that 0.5 µg HA of inactivated virus formulated with PELC induced greater HI and VN activities than 5 µg HA of virus alone. The use of an adjuvanted, low dose, whole-virus influenza vaccine will open the possibility of increasing the number of vaccine doses from the same pool. T-cell proliferation as well as IFN-g and IL-4 secretions were also significantly enhanced in the PELC-formulated 0.5 µg HA group, which indicated that this vaccination approach might enhance protective immunity in the elderly. Taken together, these results demonstrated that PELC may have applications in antigen economization and preparation for an influenza pandemic.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of enhancing a body's response to an immunogen, comprising:
    immunizing a subject in need thereof with a vaccine composition in a W/O/W emulsion wherein the emulsion does not contain poloxamers comprising:
    (a) an antigen; and
    (b) an adjuvant composition in a W/O/W emulsion, comprising:
        (i) a continuous aqueous phase comprising $H_2O$;
        (ii) an oil phase dispersed in the continuous aqueous phase, comprising:
            (1) oil;
            (1) an internal aqueous phase comprising $H_2O$, being dispersed in the oil; and
        (2) a physiologically acceptable lipophilic emulsifier selected from the group consisting of mannide monooleate and sorbitan esters, stabilizing the interface between the inner aqueous phase and the oil to form a water-in-oil (W/O) emulsion; and
        (iii) poly(ethylene glycol)-block-poly(lactide-co-ε-caprolactone), stabilizing the interface between the oil phase and the continuous aqueous phase.

2. The method of claim 1, wherein the antigen is an influenza antigen.

3. The method of claim 2, wherein the influenza antigen is an inactivated H5N1 virus.

4. The method of claim 1, prior to the immunizing step further comprising:
    preparing the adjuvant composition in the W/O/W emulsion, comprising:
    (a) dissolving the poly(ethylene glycol)-block-poly(lactide-co-ε-caprolactone) in a buffered saline;
    (b) providing a mixture comprising the oil and the physiologically acceptable lipophilic emulsifier; and
    (c) emulsifying the poly(ethylene glycol)-block-poly(lactide-co-ε-caprolactone) in the buffered saline with the oil mixture to form the adjuvant composition in the W/O/W emulsion; and
    admixing the adjuvant composition with the antigen to form the vaccine composition.

5. The method of claim 4, further comprising:
    placing the adjuvant composition in storage until ready for the immunizing step.

6. The method of claim 1, wherein the antigen is dispersed in the continuous aqueous phase.

7. The method of claim 4, wherein the adjuvant composition remains the W/O/W emulsion for at least 6 months when stored at 4° C.

8. The method of claim 4, wherein the adjuvant composition remains the W/O/W emulsion for at least 2 months when stored at 37° C.

9. A method of enhancing a body's response to an immunogen, comprising:
    immunizing a subject in need thereof a vaccine composition in an oil-in-water (O/W) emulsion comprising:
    (a) an antigen; and
    (b) an adjuvant composition in an O/W emulsion, comprising:
        (i) a continuous aqueous phase comprising $H_2O$;
        (ii) an oil phase comprising oil dispersed in the continuous aqueous phase, and
        (iii) poly(ethylene glycol)-block-poly(lactide-co-ε-caprolactone), stabilizing the interface between the oil phase and the continuous aqueous phase and wherein the adjuvant composition is without a lipophilic emulsifier.

10. The method of claim 9, prior to the immunizing step further comprising:
    preparing the adjuvant composition in the O/W emulsion, comprising:
    dissolving the poly(ethylene glycol)-block-poly(lactide-co-ε-caprolactone) in a buffered saline;
    providing the oil;
    admixing the dissolved poly(ethylene glycol)-block-poly(lactide-co-ε-caprolactone) in the buffered saline with the oil to form a mixture; and
    homogenizing the mixture to obtain the adjuvant composition in the O/W emulsion; and
    admixing the adjuvant composition with the antigen to form the vaccine composition.

11. The method of claim 1, prior to the immunizing step further comprising:
preparing the vaccine composition, comprising:
(a) dissolving the poly(ethylene glycol)-block-poly(lactide-co-ϵ-caprolactone) and the antigen in a buffered saline;
(b) providing a mixture comprising the oil and the physiologically acceptable lipophilic emulsifier; and
(c) emulsifying the poly(ethylene glycol)-block-poly(lactide-co-ϵ-caprolactone) and the antigen in the buffered saline with the oil mixture to form the vaccine composition in the W/O/W emulsion.

12. A composition in a W/O/W emulsion wherein the emulsion does not contain poloxamers, comprising:
(a) a continuous aqueous phase comprising $H_2O$;
(b) an oil phase, dispersed in the continuous aqueous phase, the oil phase comprising:
(i) oil;
(ii) an internal aqueous phase, being dispersed in the oil; and
(iii) a physiologically acceptable lipophilic emulsifier selected from the group consisting of mannide monooleate and sorbitan esters, stabilizing the interface between the inner aqueous phase and the oil to form a water-in-oil (W/O) emulsion; and
(c) poly(ethylene glycol)-block-poly(lactide-co-ϵ-caprolactone), stabilizing the interface between the oil phase and the continuous aqueous phase.

13. The composition of claim 12, which is characterized by staving stable as a W/O/W emulsion for at least 6 months when stored at 4° C.

14. The composition of claim 12, which is characterized by staying stable as a W/O/W emulsion for at least 2 months when stored at 37° C.

15. The composition of claim 12, further comprising an antigen.

16. The composition of claim 15, wherein the antigen is in the continuous aqueous phase.

17. The composition of claim 15, wherein the antigen is dissolved in the internal aqueous phase of the oil phase.

18. A method for preparing the composition of claim 12, comprising:
(a) dissolving the poly(ethylene glycol)-block-poly(lactide-co-ϵ-caprolactone) in a buffered saline;
(b) providing an oil mixture comprising the oil and the physiologically acceptable lipophilic emulsifier; and
(c) emulsifying the poly(ethylene glycol)-b lock-poly(lactide-co-ϵcaprolactone) in the buffered saline with the oil mixture to form the composition in the W/O/W emulsion.

* * * * *